(12) United States Patent
Klingler et al.

(10) Patent No.: US 7,745,443 B2
(45) Date of Patent: Jun. 29, 2010

(54) INHIBITORS OF THE GPIB-VWF INTERACTION, THEIR PREPARATION AND USE

(75) Inventors: Otmar Klingler, Rodgau (DE); Melitta Just, Langen (DE); Kuniya Sakurai, Chigasaki (JP); Naoyuki Fukuchi, Yokohama (JP)

(73) Assignees: Sanofi-Aventis Deutschland GmbH, Frankfurt (DE); Ajinomoto Co., Inc., Kawasaki (JP)

( * ) Notice: Subject to any disclaimer, the term of this patent is extended or adjusted under 35 U.S.C. 154(b) by 22 days.

(21) Appl. No.: 11/731,978

(22) Filed: Apr. 2, 2007

(65) Prior Publication Data

US 2007/0173489 A1 Jul. 26, 2007

Related U.S. Application Data

(62) Division of application No. 10/454,939, filed on Jun. 4, 2003, now Pat. No. 7,235,558.

(60) Provisional application No. 60/416,953, filed on Oct. 8, 2002.

(30) Foreign Application Priority Data

Jun. 6, 2002 (EP) .................................. 02012590

(51) Int. Cl.
C07D 215/46 (2006.01)
(52) U.S. Cl. .................. 514/255.05; 514/313; 514/339; 514/367; 514/394; 544/405; 546/159; 546/268.1; 548/159; 548/304.7
(58) Field of Classification Search ............ 514/255.05, 514/313, 339, 367, 394; 544/405; 546/159, 546/268.1; 548/159, 304.7
See application file for complete search history.

(56) References Cited

U.S. PATENT DOCUMENTS 5,919,776 A 7/1999 Hagmann et al.

FOREIGN PATENT DOCUMENTS

EP 0 614 664 A1 9/1994
EP 1 074 564 A1 * 2/2001
WO WO 98/27815 7/1998
WO WO 99/48492 * 9/1999

OTHER PUBLICATIONS

Kageyama et al. "Anti-human vWF Monoclonal Antibody, AJvW-2 Fab, Inhibits Repetitive Coronary Artery Thrombosis without Bleeding Time Prolongation in Dogs" Thrombosis Research, 2001, vol. 101, pp. 395-404.*
Bundgaard, "Novel Chemical Approaches in Prodrug Design," *Drugs of the Future* 16:443-458 (1991).
Fleisher et al., "Improved Oral Drug Delivery: Solubility Limitations Overcome by the Use of Prodrugs," *Advanced Drug Delivery Reviews* 19:115-130 (1996).
Lanza et al., "Substituted 4,6,-Diaminoquinolines as Inhibitors of C5a Receptor Binding," *M. Med. Chem.* 35:252-258 (1992).
Kageyama et al., "Anti-Human vWF Monoclonal Antibody, AjvW-2 Fab, Inhibits Repetitive Coronary Artery Thromobosis Without Bleeding Time Prolongation in Dogs," *Thrombosis Research* 101:395-404 (2001).
Raynes et al., "Novel Bisquinoline Antimalarials," *Biochemical Pharmacology* 551-559 (1996).
Trebst, A., "Measurement of Hill Reactions and Photoreduction," *Meth Enzymol.* 24:146-165 (1972).

* cited by examiner

*Primary Examiner*—Joseph R Kosack
(74) *Attorney, Agent, or Firm*—Clark & Elbing LLP

(57) ABSTRACT

The present invention relates to compounds of the formula I, (I)

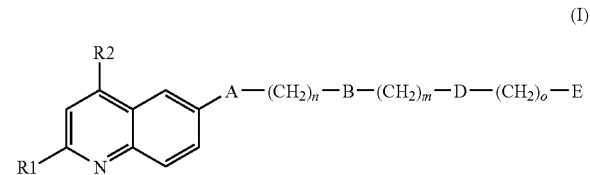

in which R1, R2, A, B, D, E, n, m or o have the meanings indicated below.

The compounds of the formula I are valuable pharmacologically active compounds. They are reversible inhibitors of the interaction between the plasma protein von Willebrand factor (vWF) and the blood platelet receptor glycoprotein Ib-IX-V complex (GPIb). They exhibit an antithrombotic effect and are suitable, for example, for the therapy and prophylaxis of atherothrombotic diseases.

7 Claims, No Drawings

INHIBITORS OF THE GPIB-VWF INTERACTION, THEIR PREPARATION AND USE

CROSS REFERENCE TO RELATED APPLICATIONS

This application is a divisional of U.S. application Ser. No. 10/454,939, filed Jun. 4, 2003, now U.S. Pat. No. 7,235,558 which claims priority from foreign patent application 02012590.2, filed Jun. 6, 2002, in Europe, and U.S. provisional application No. 60/416,953, filed Oct. 8, 2002, each of which is herein incorporated by reference.

BACKGROUND OF THE INVENTION

The present invention relates to compounds of the formula I,

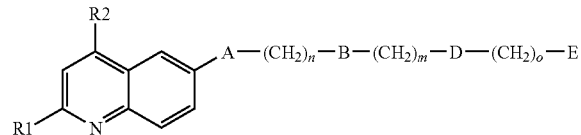

(I)

in which R1, R2, A, B, D, E, n, m or o have the meanings indicated below.

The compounds of the formula I are valuable pharmacologically active compounds. They are reversible inhibitors of the interaction between the plasma protein von Willebrand factor (vWF) and the blood platelet receptor glycoprotein Ib-IX-V complex (GPIb). This interaction causes primary adhesion of platelets to the injured subendothelial matrix and consequently platelet aggregation and thrombus formation. Inhibitors of this intraction exhibit an antithrombotic effect and are suitable, for example, for the therapy and prophylaxis of atherothrombotic diseases (for example: prevention of myocardial infarction, unstable angina, acute coronary syndromes, coronary artery disease, reocclusion following coronary thrombolysis, occlusion during thromboplasty and coronary restenosis, stroke, transient ischemic attacks, pulmonary embolism, left ventricular dysfunction, secondary prevention of clinical vascular complications in patients with cardiovascular and cerebrovascular disease, atherosclerosis, comedication to vascular interventional strategies, etc.). They can in general be applied in conditions in which the interaction between GPIb and vWF leads to undesired physiological impact or for the cure or prevention of which an inhibition of the interaction between GPIb and vWF is intended. WO 98/27815 discloses particular aminoquinolines as modulators of chemokine receptor activity for modulating eosinophil and/or lymphocyte function for the prevention and/or treatment of inflammatory and immunoregulatory disorders and diseases as well as autoimmune pathologies. The invention furthermore relates to processes for the preparation of compounds of the formula I, their use, in particular as active ingredients in pharmaceuticals, and pharmaceutical preparations comprising them.

Platelet adhesion and thrombus formation are complex processes crucial to haemostasis. The formation of a blood clot is normally the result of tissue injury which initiates the platelet adhesion/aggregation and the coagulation cascade and has the effect of slowing or preventing blood flow in wound healing. However, in certain disease states the formation of blood clots within the circulatory system reaches an undesired extent and is itself the source of morbidity potentially leading to pathological consequences.

Many adhesive proteins and various receptors are involved in this complex progress. Circulating platelets become adherent and form an occlusive thrombus either by exposure to atherosclerotic lesions following plaque rupture or in response to pathological shear stress. An important adhesive plasma protein is vWF, a multimeric glycoprotein with a mature subunit of 2050 amino acids.

Two platelet membrane glycoprotein receptors for vWF have been identified. Unactivated platelets bind vWF through the platelet GPIb complex. This interaction is induced physiologically by high shear or by binding of vWF to any surface. Subsequently vWF changes the conformation of the binding domain in such a way that interaction becomes possible. After activation, platelets express a second binding site for vWF, the GPIIb-IIIa complex, which is also a binding site for fibrinogen. Platelet activation induces amplification mechanisms which finally lead to a firm platelet attachment.

The essential role of GPIb in platelet adhesion was established with the use of antibodies and by observations on a genetic defect the Bernard-Soulier syndrome in which GPIb is absent from platelets. Platelets from Bernard-Soulier patients poorly adhere and moderately aggregate in response to vWF. Also a lot of snake venom proteins are reported which modulate the interaction of GPIb and vWF.

Specific inhibition of the interaction of GPIb to vWF using monoclonal antibodies or snake venom proteins is an effective means of controlling thrombus formation caused by arterial injury or thrombotic complications. There is also experimental evidence suggesting that inhibition of the GPIb-vWF interaction inhibits thrombus formation with a wider safety window than abciximab an antibody for GPIIb-IIIa which is already launched (Kageyama, S.; Yamamoto, H.; Nakazawa, H., Yoshimoto, R. Thromb. Res. 101 (2001) 395-404). However these type of drugs are only qualified for an intravenous application.

There continues to be a need for safe and effective therapeutic antithrombotic agents to limit or prevent thrombus formation. It is most desirable to develop agents that inhibit an early step in thrombogenesis like inhibition of the GPIb-vWF interaction. A specific inhibitor for the GPIb-vWF interaction which is suitable for oral long term use would have substantial practical value in the practice of medicine.

The present invention satisfies the above needs by providing novel compounds of the formula I, which are low molecular weight compounds and inhibit the GPIb-vWF interaction.

Thus, the present invention relates to compounds of the formula I,

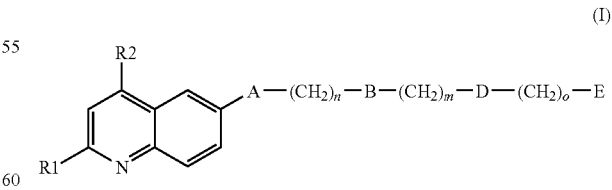

(I)

wherein
n is the integer zero, 1, 2, 3 or 4;
m is the integer zero, 1, 2, 3 or 4;
o is the integer zero, 1, 2, 3 or 4;
R1 is —($C_1$-$C_8$)-alkyl;
R2 is —$NR^4R^5$, wherein $R^4$ and $R^5$ are identical or different and are hydrogen atom or —$(C_1-C_8)$-alkyl;

A is —NH—CO— or —CO—NH—;

B is 1. a covalent bond,
2. a monocyclic or bicyclic 6- to 14-membered aryl, wherein aryl is unsubstituted or mono-, di-, tri- or tetrasubstituted independently of one another by $R^3$,
3. $(C_3-C_8)$-cycloalkyl or
4. Het, wherein Het is unsubstituted or mono-, di-, tri- or tetrasubstituted independently of one another by $R^3$, D is —NH—CO—, —CO—NH— or —NH—;

E is a monocyclic or bicyclic 6- to 14-membered aryl, wherein aryl is unsubstituted or mono-, di-, tri- or tetrasubstituted independently of one another by $R^3$, or Het wherein Het is a saturated, partially unsaturated or aromatic monocyclic or bicyclic heterocyclic ring system containing 3 to 10 ring atoms of which 1, 2, 3 or 4 are identical or different heteroatoms selected from the series consisting of nitrogen, oxygen and sulfur and wherein Het is unsubstituted or mono-, di-, tri- or tetrasubstituted independently of one another by $R^3$;

with the proviso that, when B is a covalent bond and Het is a bicyclic heterocyclic ring system, the ring of Het to which -D-$(CH_2)_o$— is attached contains at least one hetero atom;

$R^3$ is 1. —$(C_1-C_8)$-alkyl,
2. $(C_1-C_8)$-alkoxy,
3. hydroxyl,
4. trifluoromethoxy,
5. trifluoromethyl,
6. halogen,
7. nitro,
8. —$NR^4R^5$, wherein $R^4$ and $R^5$ are as defined above,
9. —$(C_1-C_8)$-alkylcarbonyl,
10. —CN,
11. aminosulfonyl-,
12. amidino,
13. guanidino,
14. tri-$((C_1-C_4)$-alkyl)ammonio-,
15. di-$((C_1-C_8)$-alkyl)amino-,
16. $(C_1-C_8)$-alkylaminosulfonyl-,
17. di-$((C_1-C_8)$-alkyl)aminosulfonyl,
18. —O-Het, wherein Het is unsubstituted or mono-, di-, tri- or tetrasubstituted independently of one another by $R^3$ and $R^3$ is as defined above under 1. to 17., or
19. Het-, wherein Het is unsubstituted or mono-, di-, tri- or tetrasubstituted independently of one another by $R^3$ and $R^3$ is as defined above under 1. to 17., in all their stereoisomeric forms and mixtures thereof in any ratio, and their physiologically tolerable salts and as further specified in the attached claims.

The present invention also relates to the compounds of the formula I, wherein n is the integer zero or 1,
m is the integer zero or 1,
o is the integer zero or 1,
R1 is —$(C_1-C_4)$-alkyl;
R2 is —$NR^4R^5$, wherein
$R^4$ and $R^5$ are identical or different and are hydrogen atom or —$(C_1-C_4)$-alkyl;

A is —NH—CO— or —CO—NH—;

B is 1. a covalent bond,
2. a monocyclic or bicyclic 6- to 14-membered aryl, wherein aryl is unsubstituted or mono-, di- or trisubstituted independently of one another by $R^3$, or
3. $(C_3-C_7)$-cycloalkyl, D is —NH—CO—, —CO—NH— or —NH—;

E is 1. aryl selected from the group phenyl, naphthyl, biphenylyl, fluorenyl and anthracenyl, wherein aryl is unsubstituted or mono-, di- or trisubstituted independently of one another by $R^3$, or
2. Het selected from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, pyridine, pyran, thiopyran, pyridazine, pyrimidine, pyrazine, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, benzo[1,4]dioxine, 4H-benzo[1,4]oxazine, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines or ring systems which result from the listed heterocycles by fusion or condensation of a carbocyclic ring, for example benzo-fused, cyclopenta-fused, cyclohexa-fused or cyclohepta-fused derivatives of these heterocycles, pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), 2,3-dihydrobenzo[1,4]dioxine, indoline, isoindoline, 3,4-dihydro-2H-benzo[1,4]oxazine, perhydro-1,4-thiazine, perhydroazepine, 1,2,3,4-tetrahydroquinoline, 1,2,3,4-tetrahydroisoquinoline and wherein Het is unsubstituted or mono-, di- or trisubstituted independently of one another by $R^3$;

$R^3$ is 1. —$(C_1-C_4)$-alkyl,
2. hydroxyl,
3. halogen,
4. —$NR^4R^5$, wherein $R^4$ and $R^5$ are as defined above,
5. aminosulfonyl-,
6. $(C_1-C_8)$-alkylaminosulfonyl-,
7. di-$((C_1-C_8)$-alkyl)aminosulfonyl,
8. —$(C_1-C_8)$-alkoxy,
9. —O-Het, wherein Het is as defined above and is unsubstituted or mono-, di- or trisubstituted independently of one another by $R^3$ and $R^3$ is as defined above under 1. to 8., or
10. Het-, wherein Het is as defined above and is unsubstituted or mono-, di- or trisubstituted independently of one another by $R^3$ and $R^3$ is as defined above under 1. to 8.

The present invention also relates to the compounds of the formula I, wherein n is the integer zero or 1,
m is the integer zero or 1,
o is the integer zero or 1,
R1 is methyl;
R2 is amino;

A is —NH—CO— or —CO—NH—;

B is phenyl, wherein phenyl is unsubstituted or mono-, di- or trisubstituted independently of one another by $R^3$, D is —NH—CO—, —CO—NH— or —NH—;

E is 1. phenyl, wherein phenyl is unsubstituted or mono-, di- or trisubstituted independently of one another by $R^3$, or
2. Het, which is selected from the group pyridine, pyrimidine, pyrazine, quinoline, benzimidazole, benzthiazole, isoquinoline, chromane, indazole, isochromane, cinnoline, quinazoline, quinoxaline, phthalazine, pyridoimidazoles, pyrroline, pyrrolidine, tetrahydropyridine, piperidine, imidazolidine, 1,3-oxazolidine, 4,5-dihydro-1,3-thiazole, 1,3-thiazolidine, piperazine, indoline, isoindoline, 1,2,3,4-tetrahydroquinoline, 1,2,3,4-tetrahydroisoquinoline and wherein Het is unsubstituted or mono-, di- or trisubstituted independently of one another by $R^3$;

$R^3$ is 1. methyl,
2. hydroxyl,
3. halogen,
4. —$NH_2$,
5. aminosulfonyl-,
6. methoxyl,
7. —O-Het, wherein Het is as defined above and is unsubstituted or mono-, di- or trisubstituted independently of one another by $R^3$ and $R^3$ is as defined above under 1. to 6., or
8. Het-, wherein Het is as defined above and is unsubstituted or mono-, di- or trisubstituted independently of one another by $R^3$ and $R^3$ is as defined above under 1. to 6.

The present invention also relates to the compounds of the formula I selected from the group 3-(2-Amino-6-methyl-pyrimidin-4-ylamino)-N-(4-amino-2-methyl-quinolin-6-yl)-propionamide, 2-Amino-4-[3-(4-amino-2-methyl-quinolin-6-ylcarbamoyl)-phenylamino]-1,6-dimethyl-pyrimidin-1-ium, 2-Amino-4-[4-(4-amino-2-methyl-quinolin-6-ylcarbamoyl)-benzylamino]-1,6-dimethyl-pyrimidin-1-ium, Pyrazine-2-carboxylic acid 4-(4-amino-2-methyl-quinolin-6-ylcarbamoyl)-benzylamide, 6-Amino-N-[4-(4-amino-2-methyl-quinolin-6-ylcarbamoyl)-benzyl]-nicotinamide, 6-Pyrrolidin-1-yl-pyrazine-2-carboxylic acid 4-(4-amino-2-methyl-quinolin-6-ylcarbamoyl)-benzylamide, 2-Amino-4-[(4-{[(4-amino-2-methyl-6-quinolinyl)-carbonyl]amino}phenyl)amino]-1,6-dimethylpyrimidin-1-ium, 2-Amino-4-[(3-{[(4-amino-2-methyl-6-quinolinyl)carbonyl]amino}phenyl)amino]-1,6-dimethylpyrimidin-1-ium, 2-Amino-4-[(4-{[(4-amino-2-methyl-6-quinolinyl)carbonyl]amino}benzyl)amino]-1,6-dimethylpyrimidin-1-ium, 2-Amino-4-[(4-{[(4-amino-2-methyl-6-quinolinyl)-carbonyl]amino}benzyl)amino]-6-methylpyrimidine, 4-Amino-N-[4-({[(6-chloro-3-pyridinyl)carbonyl]amino}methyl)phenyl]-2-methyl-6-quinolinecarboxamide, 4-Amino-2-methyl-N-(4-{[(2-pyridinylcarbonyl)amino]methyl}phenyl)-6-quinoline-carboxamide, 4-Amino-N-[4-({[(2-chloro-4-pyridinyl)carbonyl]amino}methyl)phenyl]-2-methyl-6-quinolinecarboxamide, 4-Amino-N-[4-({[(3-bromo-5-pyridinyl)carbonyl]-amino}methyl)phenyl]-2-methyl-6-quinolinecarboxamide, 4-Amino-N-[4-({[(3-amino-2-pyrazinyl)carbonyl]amino}methyl)phenyl]-2-methyl-6-quinolinecarboxamide, 4-Amino-N-{4-[(2-pyridinylcarbonyl)amino]phenyl}-2-methyl-6-quinolinecarboxamide, 4-Amino-N-{4-[(3-pyridinylcarbonyl)amino]phenyl}-2-methyl-6-quinoline-carboxamide, 4-Amino-N-(4-{[(2-chloro-3-pyridinyl)carbonyl]amino}phenyl)-2-methyl-6-quinolinecarboxamide, 4-Amino-N-(4-{[(5-bromo-3-pyridinyl)carbonyl]-amino}phenyl)-2-methyl-6-quinolinecarboxamide, 4-Amino-N-(4-{[(2-amino-3-pyrazinyl)carbonyl]amino}phenyl)-2-methyl-6-quinolinecarboxamide, 4-Amino-N-(4-{[(2-amino-3-pyridinyl)carbonyl]amino}phenyl)-2-methyl-6-quinolinecarboxamide, 4-Amino-N-(4-{[(2-amino-5-pyridinyl)carbonyl]amino}phenyl)-2-methyl-6-quinolinecarboxamide, 4-Amino-N-(4-{[(2-hydroxy-5-pyridinyl)carbonyl]amino}phenyl)-2-methyl-6-quinolinecarboxamide, 4-Amino-N-(4-{[(2-pyrazinyl)carbonyl]-amino}phenyl)-2-methyl-6-quinolinecarboxamide, 4-Amino-N-(4-{[(2,3-dichloro-5-pyridinyl)carbonyl]amino}phenyl)-2-methyl-6-quinolinecarboxamide, 4-Amino-N-(4-{[3-(aminosulfonyl)-4-chlorobenzoyl]amino}phenyl)-2-methyl-6-quinolinecarbox-amide, 4-Amino-N-{4-[(3-dimethylaminobenzoyl)amino]phenyl}-2-methyl-6-quinolinecarboxamide, 4-Amino-N-(4-{[(2-methyl-1H-benzimidazol-5-yl)carbonyl]-amino}phenyl)-2-methyl-6-quinolinecarboxamide, 4-Amino-N-(4-{[4-(4-piperidinyloxy) benzoyl]amino}phenyl)-2-methyl-6-quinolinecarboxamide, 4-Amino-N-(4-{[(2-amino-1H-benzimidazol-5-yl)carbonyl]amino}phenyl)-2-methyl-6-quinolinecarboxamide, 4-Amino-N-(4-{[(2-amino-1,2-benzthiazol-6-yl)carbonyl]-amino}phenyl)-2-methyl-6-quinolinecarboxamide, 4-amino-N-{4-[(1H-benzimidazol-5-ylcarbonyl)amino]phenyl}-2-methyl-6-quinolinecarboxamide, 4-Amino-N-(4-{[(2-amino-6-quinolinyl)carbonyl]amino}phenyl)-2-methyl-6-quinolinecarboxamide, 4-Amino-N-(4-{[(2-amino-6-quinolinyl)carbonyl]amino}-2-methoxyphenyl)-2-methyl-6-quinolinecarboxamide, 4-Amino-N-(2-methoxy-4-{[(2-methyl-1H-benzimidazol-5-yl)carbonyl]amino}phenyl)-2-methyl-6-quinolinecarboxamide, 1,4-Di-{[(3-amino-2-methylquinolin-6-yl)carbonyl]amino}benzene, 4-Amino-N-{4-[(1H-indazol-6-ylamino)methyl]phenyl}-2-methyl-6-quinolinecarboxamide, 4-Amino-N-(4-{[(2-amino-1,3-benzothiazol-6-yl)carbonyl]amino}cyclohexyl)-2-methyl-6-quinolinecarboxamide and 4-Amino-N-(4-{[(2-amino-6-quinolinyl)carbonyl]amino}-cyclohexyl)-2-methyl-6-quinolinecarboxamide.

In general, the meaning of any group, residue, heteroatom, number etc. which can occur more than once in the compounds of the formula I, is independent of the meaning of this group, residue, heteroatom, number etc. in any other occurrence. All groups, residues, heteroatoms, numbers etc. which can occur more than once in the compounds of the formula I can be identical or different.

As used herein, the term alkyl is to be understood in the broadest sense to mean hydrocarbon residues which can be linear, i. e. straight-chain, or branched and which can be acyclic or cyclic residues or comprise any combination of acyclic and cyclic subunits. Further, the term alkyl as used herein expressly includes saturated groups as well as unsaturated groups which latter groups contain one or more, for example one, two or three, double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of alkyl residues containing 1, 2, 3, 4, 5, 6, 7 or 8 carbon atoms are methyl, ethyl, propyl, butyl, pentyl, hexyl, heptyl or octyl, the n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tert-pentyl, sec-butyl, tert-butyl or tert-pentyl.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl, or alkynyl residues such as ethynyl, 1-propynyl, 2-propynyl (=propargyl) or 2-butynyl. Alkyl residues can also be unsaturated when they are substituted.

Examples of cyclic alkyl residues are cycloalkyl residues containing 3, 4, 5 or 6 ring carbon atoms like cyclopropyl, cyclobutyl, cyclopentyl or cyclohexyl, which can also be substituted and/or unsaturated. Unsaturated cyclic alkyl groups and unsaturated cycloalkyl groups like, for example, cyclopentenyl or cyclohexenyl can be bonded via any carbon atom.

Of course, a cyclic alkyl group has to contain at least three carbon atoms, and an unsaturated alkyl group has to contain at least two carbon atoms. Thus, a group like $(C_1-C_8)$-alkyl is to be understood as comprising, among others, saturated acyclic $(C_1-C_8)$-alkyl, $(C_3-C_6)$-cycloalkyl, and unsaturated $(C_2-C_8)$-alkyl like $(C_2-C_8)$-alkenyl or $(C_2-C_8)$-alkynyl. Similarly, a group like $(C_1-C_4)$-alkyl is to be understood as comprising, among others, saturated acyclic $(C_1-C_4)$-alkyl, and unsaturated $(C_2-C_4)$-alkyl like $(C_2-C_4)$-alkenyl or $(C_2-C_4)$-alkynyl.

Unless stated otherwise, the term alkyl preferably comprises acyclic saturated hydro-carbon residues which have from one to six carbon atoms and which can be linear or branched. A particular group of saturated acyclic alkyl residues is formed by $(C_1-C_4)$-alkyl residues like methyl, ethyl, n-propyl, isopropyl, n-butyl, isobutyl, sec-butyl and tBu.

Unless stated otherwise, and irrespective of any specific substituents bonded to alkyl groups which are indicated in the definition of the compounds of the formula I, alkyl groups can in general be unsubstituted or substituted by one or more, for example one, two or three, identical or different substituents. Any kind of substituents present in substituted alkyl residues can be present in any desired position provided that the substitution does not lead to an unstable molecule. Examples of substituted alkyl residues are alkyl residues in which one or more, for example 1, 2 or 3, hydrogen atoms are replaced with halogen atoms, in particular fluorine atoms.

The term aryl refers to a monocyclic or polycyclic hydrocarbon residue in which at least one carbocyclic ring is present that has a conjugated pi electron system. In a $(C_6-C_{14})$-aryl group from 6 to 14 ring carbon atoms are present. Examples of $(C_6-C_{14})$-aryl groups are phenyl, naphthyl, biphenylyl, fluorenyl or anthracenyl. Examples of $(C_6-C_{10})$-aryl groups are phenyl or naphthyl. Unless stated otherwise, and irrespective of any specific substituents bonded to aryl groups which are indicated in the definition of the compounds of the formula I, aryl groups, for example phenyl, naphthyl or fluorenyl, can in general be unsubstituted or substituted by one or more, for example one, two, three or four, identical or different substituents. Aryl groups can be bonded via any desired position, and in substituted aryl groups the substituents can be located in any desired position.

In monosubstituted phenyl groups the substituent can be located in the 2-position, the 3-position or the 4-position. If a phenyl group carries two substituents, they can be located in 2,3-position, 2,4-position, 2,5-position, 2,6-position, 3,4-position or 3,5-position. In phenyl groups carrying three substituents the substituents can be located in 2,3,4-position, 2,3,5-position, 2,3,6-position, 2,4,5-position, 2,4,6-position, or 3,4,5-position. Naphthyl groups can be 1-naphthyl and 2-naphthyl. In substituted naphthyl groups the substituents can be located in any positions, for example in monosubstituted 1-naphthyl groups in the 2-, 3-, 4-, 5-, 6-, 7-, or 8-position and in monosubstituted 2-naphthyl groups in the 1-, 3-, 4-, 5-, 6-, 7-, or 8-position. Biphenylyl groups can be biphenyl-2-yl, biphenyl-3-yl or biphenyl-4-yl. Fluorenyl groups can be bonded via the 1-, 2-, 3-, 4- or 9-position. In monosubstituted fluorenyl groups bonded via the 9-position the substituent is preferably present in the 1-, 2-, 3- or 4-position.

The above statements relating to aryl groups correspondingly apply to divalent groups derived from aryl groups, i. e. to arylene groups like phenylene which can be unsubstituted or substituted 1,2-phenylene, 1,3-phenylene or 1,4-phenylene, or naphthylene which can be unsubstituted or substituted 1,2-naphthalenediyl, 1,3-naphthalenediyl, 1,4-naphthalenediyl, 1,5-naphthalenediyl, 1,6-naphthalenediyl, 1,7-naphthalenediyl, 1,8-naphthalenediyl, 2,3-naphthalenediyl, 2,6-naphthalenediyl or 2,7-naphthalenediyl.

The Het group comprises groups containing 3, 4, 5, 6, 7, 8, 9 or 10 ring atoms in the parent monocyclic or bicyclic heterocyclic ring system. In monocyclic Het groups the heterocyclic ring preferably is a 3-membered, 4-membered, 5-membered, 6-membered or 7-membered ring, particularly preferably a 5-membered or 6-membered ring. In bicyclic Het groups preferably two fused rings are present one of which is a 5-membered ring or 6-membered heterocyclic ring and the other of which is a 5-membered or 6-membered heterocyclic or carbocyclic ring, i. e. a bicyclic ring Het preferably contains 8, 9 or 10 ring atoms, particularly preferably 9 or 10 ring atoms.

Het comprises saturated heterocyclic ring systems which do not contain any double bonds within the rings, as well as unsaturated heterocyclic ring systems including mono-unsaturated and poly-unsaturated heterocyclic ring systems which contain one or more, for example one, two, three, four or five, double bonds within the rings provided that the resulting system is stable. Unsaturated rings may be partially unsaturated or non-aromatic, or they may be aromatic, i. e. double bonds within the rings in the Het group may be arranged in such a manner that a conjugated pi electron system results. Aromatic rings in a Het group may be 5-membered or 6-membered rings, i. e. aromatic groups in a Het group contain 5 to 10 ring atoms. Aromatic rings in a Het group thus comprise 5-membered and 6-membered monocyclic heterocycles and bicyclic heterocycles composed of two 5-membered rings, one 5-membered ring and one 6-membered ring, or two 6-membered rings. In bicyclic aromatic groups in a Het group one or both rings may contain heteroatoms. Aromatic Het groups may also be referred to by the customary term heteroaryl for which all the definitions and explanations above and below relating to Het correspondingly apply.

In a Het group preferably 1 or 2 identical or different ring heteroatoms selected from nitrogen, oxygen and sulfur atoms are present. In general, the ring heteroatoms can be present in any desired combination and in any desired positions with respect to each other provided that the resulting heterocyclic system is known in the art and is stable and suitable as a subgroup in a drug substance. Examples of parent structures of heterocycles from which the Het group any other heterocyclic groups can be derived are aziridine, oxirane, azetidine, pyrrole, furan, thiophene, dioxole, imidazole, pyrazole, oxazole, isoxazole, thiazole, isothiazole, 1,2,3-triazole, 1,2,4-triazole, pyridine, pyran, thiopyran, pyridazine, pyrimidine, pyrazine, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, benzo[1,4]dioxine, 4H-benzo[1,4]oxazine, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines, etc. as well as ring systems which result from the listed heterocycles by fusion (or condensation) of a carbocyclic ring, for example benzo-fused, cyclopenta-fused, cyclohexa-fused or cyclohepta-fused derivatives of these heterocycles.

The fact that many of the before-listed names of heterocycles are the chemical names of unsaturated or aromatic ring systems does not imply that the Het groups and other heterocyclic groups could only be derived from the respective unsaturated ring system. The names here only serve to describe the ring system with respect to ring size and the number of the heteroatoms and their relative positions. As explained above, for example a Het group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which a Het group and any other heterocyclic group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), 2,3-dihydrobenzo[1,4]dioxine, 3,4-dihydro-2H-benzo[1,4]oxazine, perhydro-1,4-thiazine (=thiomorpholine), perhydroazepine, indoline, isoindoline, 1,2,3,4-tetrahydroquinoline, 1,2,3,4-tetrahydroisoquinoline, etc.

The Het group and other any other heterocyclic group may be bonded via any ring carbon atom, and in the case of nitrogen heterocycles via any suitable ring nitrogen atom, if applicable. Thus, for example, a pyrrolyl group can be pyrrol-1-yl, pyrrol-2-yl or pyrrol-3-yl, a pyrrolidinyl group can be pyrrolidin-1-yl (=pyrrolidino), pyrrolidin-2-yl or pyrrolidin-3-yl, a pyridinyl group can be pyridin-2-yl, pyridin-3-yl or pyridin-4-yl, a piperidinyl group can be piperidin-1-yl (=piperidino), piperidin-2-yl, piperidin-3-yl or piperidin-3-yl. Furyl can be furan-2-yl or fur-3-yl, thienyl can be thiophen-2-yl or thiophen-3-yl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=pyrimidin-6-yl) or pyrimidin-5-yl, piperazinyl can be piperazin-1-yl (=piperazin-4-yl=piperazino) or piperazin-2-yl. Indolyl can be indol-1-yl, indol-2-yl, indol-3-yl, indol-4-yl, indol-5-yl, indol-6-yl or indol-7-yl. Similarly benzimidazolyl, benzoxazolyl and benzothiazol groups can be bonded via the 2-position and via any of the positions 4, 5, 6, and 7. Quinolinyl can be quinolin-2-yl, quinolin-3-yl, quinolin-4-yl, quinolin-5-yl, quinolin-5-yl, quinolin-7-yl or quinolin-8-yl, isoqinolinyl can be isoquinolin-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

Unless stated otherwise, and irrespective of any specific substituents in aryl groups, Het groups or any other heterocyclic groups which are indicated in the definition of the compounds of the formula I, aryl groups, Het groups and other heterocyclic groups can be unsubstituted or substituted on ring carbon atoms with one or more, for example one, two, three or four, identical or different substituents like $(C_1-C_4)$-alkyl, $(C_1-C_4)$-alkyloxy, halogen, nitro, amino, $(C_1-C_4)$-alkylamino, di-$((C_1-C_4)$-alkyl)amino, trifluoromethyl, trifluoromethoxy, hydroxy, oxo, hydroxymethyl, methylenedioxy, ethylenedioxy, cyano, methylsulfonyl, etc.

The substituents can be present in any desired position provided that a stable molecule results. Preferably not more than two nitro groups are present in the compounds of the formula I.

Further, unless stated otherwise, and irrespective of any specific substituents in Het groups or any other heterocyclic groups which are indicated in the definition of the compounds of the formula I, Het groups and other heterocyclic groups can on each suitable ring nitrogen atom independently of one another be unsubstituted, i. e. carry a hydrogen atom, or be substituted, for example, by $(C_1-C_8)$-alkyl, for example $(C_1-C_4)$-alkyl such as methyl or ethyl, optionally substituted phenyl, phenyl-$(C_1-C_4)$-alkyl, for example benzyl. Suitable nitrogen heterocycles can also be present as quaternary salts.

The explanations relating to the Het group correspondingly apply to divalent Het groups including divalent heteroaromatic groups which may be bonded via any two ring carbon atoms and in the case of nitrogen heterocycles via any carbon atom and any suitable ring nitrogen atom or via any two suitable nitrogen atoms. For example, a pyridinediyl group can be pyridin-2,3-diyl, pyridin-2,4-diyl, pyridin-2,5-diyl, pyridin-2,6-diyl, pyridin-3,4-diyl or pyridin-3,5-diyl, a piperidinediyl group can be, among others, piperidin-1,2-diyl, piperidin-1,3-diyl, piperidin-1,4-diyl, piperidin-2,3-diyl, piperidin-2,4-diyl or piperidin-3,5-diyl, a piperazinediyl group can be, among others, piperazin-1,3-diyl, piperazin-1,4-diyl, piperazin-2,3-diyl, piperazin-2,5-diyl, etc.

Halogen is fluorine, chlorine, bromine or iodine, preferably fluorine, chlorine or bromine.

Physiologically tolerable salts of the compounds of formula I are nontoxic salts that are physiologically acceptable, in particular pharmaceutically utilizable salts. Such salts of compounds of the formula I containing acidic groups, for example a carboxy group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formula I, for example amino groups or amidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid. The present invention also includes acid addition salts of compounds of the formula I which contain, for example, two basic groups, with one or two acid equivalents.

Salts of compounds of the formula I can be obtained by customary methods known to those skilled in the art, for example by combining a compound of the formula I with an inorganic or organic acid or base in a solvent or diluent, or from other salts by cation exchange or anion exchange. The present invention also includes all salts of the compounds of the formula I which, because of low physiologically tolerability, are not directly suitable for use in pharmaceuticals but are suitable, for example, as intermediates for carrying out further chemical modifications of the compounds of the formula I or as starting materials for the preparation of physiologically tolerable salts.

The anions of the mentioned acids that may be present in acid addition salts of the compounds of the formula I, are also examples of anions that may be present in the compounds of the formula I if they contain one or more positively charged groups like trialkylammonio-substituents, i. e. groups of the formula (alkyl)3N+ bonded via the positively charged nitrogen atom, representing $R^3$, or quaternized ring nitrogen atoms in heterocyclic groups. In general a compound of the formula I contains one or more physiologically tolerable anions or anion equivalents as counterions if it contains one or more permanently positively charged groups like trialkylammonio.

Optically active carbon atoms present in the compounds of the formula I can independently of each other have R configuration or S configuration. The compounds of the formula I can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formula I, and it comprises all ratios of the stereoisomers in the mixtures. In case the compounds of the formula I can be present as E isomers or Z isomers (or cis isomers or trans isomers) the invention relates both to pure E isomers and pure Z isomers and to E/Z mixtures in all ratios. The invention also comprises all tautomeric forms of the compounds of the formula I.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formula I can also be obtained by employing stereochemically uniform starting materials or by using stereoselective reactions.

The invention also includes derivatives and modifications of the compounds of the formula I, for example prodrugs, protected forms and other physiologically tolerable derivatives, as well as active metabolites of the compounds of the formula I. The invention relates in particular to prodrugs and protected forms of the compounds of the formula I which can be converted into compounds of the formula I under physiological conditions. Suitable prodrugs for the compounds of the formula I, i. e. chemically modified derivatives of the compounds of the formula I having properties which are improved in a desired manner, for example with respect to solubility, bioavailability or duration of action, are known to those skilled in the art. More detailed information relating to prodrugs is found in standard literature like, for example, Design of Prodrugs, H. Bundgaard (ed.), Elsevier, 1985, Fleisher et al., Advanced Drug Delivery Reviews 19 (1996) 115-130; or H. Bundgaard, Drugs of the Future 16 (1991) 443 which are all incorporated herein by reference. Suitable prodrugs for the compounds of the formula I are especially acyl prodrugs and carbamate prodrugs of acylatable nitrogen-containing groups such as amino groups and the guanidino group and also ester prodrugs and amide prodrugs of carboxylic acid groups which may be present in compounds of the formula I. In the acyl prodrugs and carbamate prodrugs one or more, for example one or two, hydrogen atoms on nitrogen atoms in such groups are replaced with an acyl group or a carbamate, preferably a $(C_1$-$C_6)$-alkyloxycarbonyl group. Suitable acyl groups and carbamate groups for acyl prodrugs and carbamate prodrugs are, for example, the groups $R^{p1}$—CO— and $R^{p2}$O—CO—, in which $R^{p1}$ is hydrogen, $(C_1$-$C_{18})$-alkyl, $(C_3$-$C_8)$-cycloalkyl, $(C_3$-$C_8)$-cycloalkyl-$(C_1$-$C_4)$-alkyl-, $(C_6$-$C_{14})$-aryl, Het-, $(C_6$-$C_{14})$-aryl-$(C_1$-$C_4)$-alkyl- or Het-$(C_1$-$C_4)$-alkyl- and in which $R^{p2}$ has the meanings indicated for $R^{p1}$ with the exception of hydrogen.

Also with respect to all preferred compounds of the formula I all their stereoisomeric forms and mixtures thereof in any ratio and their physiologically acceptable salts explicitly are a subject of the present invention, as well as are their prodrugs. Similarly, also in all preferred compounds of the formula I all residues that are present more than one time in the molecule are independent of each other and can be identical or different.

The present invention also relates to processes of preparation by which the compounds of the formula I are obtainable. The compounds of the formula I can generally be prepared by linkage of two or more fragments (or building blocks) which can be derived retrosynthetically from the formula I. In the preparation of the compounds of the formula I it can generally be advantageous or necessary in the course of the synthesis to introduce functional groups which could lead to undesired reactions or side reactions in a synthesis step in the form of precursors which are later converted into the desired functional groups. As examples of precursor groups cyano groups may be mentioned which may later be converted into amidino groups, or nitro groups which may be converted into amino groups. Protecting groups (or blocking groups) that may be present on functional groups include allyl, tert-butyl, benzyl, allyloxycarbonyl (Alloc), tert-butoxycarbonyl (Boc), benzyloxycarbonyl (Z) and 9-fluorenylmethoxycarbonyl (Fmoc) as protecting groups for hydroxy, carboxylic acid, amino, amidino and guanidino groups.

In particular, in the preparation of the compounds of the formula I building blocks can be connected by performing one or more condensation reactions and/or substitution reactions such as amide couplings, i. e. by forming an amide bond between a carboxylic acid group of one building block and an amino group of another building block, or by a nucleophilic substitution of a leaving group of one building block by an nucleophilic group of another building block, i. e. by substitution of an halogen of one building block by an amino group of another building block. For example, compounds of the formula I can be prepared by linking the building blocks of the formulae II, III, and IV

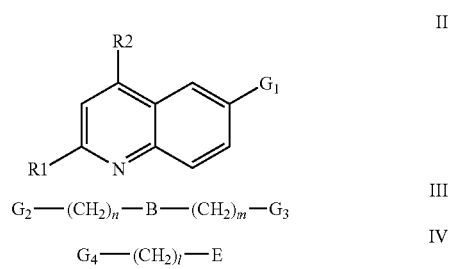

by means of forming in a manner known per se an amide bond between the carboxylic acid group G1 depicted in formula II and the $NH_2$ group G2 depicted in formula III or between the carboxylic acid group G2 depicted in formula III and the $NH_2$ group G1 depicted in formula II or by means of forming in a manner known per se an amide bond between the carboxylic acid group G3 depicted in formula III and the $NH_2$ group G4 depicted in formula IV or. between the carboxylic acid group G4 depicted in formula IV and the $NH_2$ group G3 depicted in formula III or by means of forming a bonding between building block of the formula III and building block of the formula IV by nucleophilic substitution of an halogen atom G4 depicted in formula IV by an amino group G3 depicted in formula III or by means of forming a bonding between building block of the formula III and building block of the formula IV by nucleophilic substitution of an halogen atom G3 depicted in formula III by an amino group G4 depicted in formula IV.

In the compounds of the formulae II, III and IV the groups and numbers m, n, o, $R^1$, $R^2$, B and E are as defined above. In general, in addition to the denotations of the groups and substituents given above, in the compounds of the formulae II, III and IV, functional groups can also be present in the form of precursor groups which are later converted into the groups present in the compounds of the formula I, or can be present in protected form.

The starting compounds of the formulae II, III and IV and other compounds which are employed in the synthesis of the compounds of formula I for introducing certain structural units, are commercially available or can be readily prepared from commercially available compounds by or analogously to procedures described below or in the literature which is readily available to those skilled in the art, i.e. building block of the formula II can be prepared by a procedure described in T. J. Lanza et al J. Med. Chem. 1992, 35, 252-258.

For the preparation of the compounds of formula I first the compounds of the formulae II and III may be linked and the resulting intermediate product then be condensed or linked with a compound of the formula IV to give a compound of the formula I. Just so, first the compounds of the formulae III and IV may be condensed or linked and the resulting intermediate product then be linked to a compound of the formula II to give a compound of the formula I. After any such reaction step in the course of such syntheses protecting and deprotecting steps and conversions of precursor groups into the desired final groups may be carried out and further modifications may be made.

Various general methods for the formation of an amide bond that can be employed in the synthesis of the compounds of formula I are just so well known to those skilled in the art, for example from peptide chemistry. An amide coupling step can favorably be carried out by employing a free carboxylic acid, i. e. a compound of the formula II or an intermediate coupling product in which a group like G1 reacting in that step is a COOH group, activating that carboxylic acid group, preferably in situ, by means of a customary coupling reagent such as a carbodiimide like dicyclohexylcarbodiimide (DCC) or diisopropylcarbodiimide (DIC), or an N,N'-carbonyldiazole like N,N'-carbonyldiimidazole, or a uronium salt like O-((cyano(ethoxycarbonyl)methylene)amino)-1,1,3,3-tetramethyluronium tetrafluoroborate (TOTU) or O-(7-azabenzotriazol-1-yl)-1,1,3,3-tetramethyluronium hexafluorophosphate (HATU), or a chloroformic acid ester like ethyl chloroformate or isobutyl chloroformate, or tosyl chloride, or propylphosphonic acid anhydride, or others, and then reacting the activated carboxylic acid derivative with an amino compound of the formula III. An amide bond can also be formed by reacting an amino compound with a carboxylic acid halide, in particular a carboxylic acid chloride, which can be prepared in a separate step or in situ from a carboxylic acid and, for example, thionyl chloride, or an carboxylic acid ester or thioester, for example a methyl ester, ethyl ester, phenyl ester, nitrophenyl ester, pentafluorophenyl ester, methylthio ester, phenylthio ester or pyridin-2-ylthio ester.

The activation reactions and coupling reactions are usually performed in the presence of an inert solvent (or diluent), for example in the presence of an aprotic solvent like dimethylformamide (DMF), tetrahydrofuran (THF), dimethylsulfoxide (DMSO), hexamethyl phosphoric triamide (HMPT), 1,2-dimethoxyethane (DME), dioxane, or others, or in a mixture of such solvents. Depending on the specific process, the reaction temperature may be varied over a wide range and be, for example, from about −20° C. to the boiling temperature of the solvent or diluent. Also depending on the specific process, it may be necessary or advantageous to add in a suitable amount one or more auxiliary agents, for example a base like a tertiary amine, such as N-ethylmorpholine, triethylamine or diisopropylethylamine, or an alkali metal alcoholate, such as sodium methoxide or potassium tert-butoxide, for adjusting the pH or neutralizing an acid that is formed or for liberating the free base of an amino compound that is employed in the form of an acid addition salt, or an N-hydroxyazole like 1-hydroxybenzotriazole, or a catalyst like 4-dimethylaminopyridine. Details on methods for the preparation of activated carboxylic acid derivatives and the formation of amide bonds and ester bonds as well as source literature are given in various standard references like, for example, J. March, Advanced Organic Chemistry, 4th ed., John Wiley & Sons, 1992; or Houben-Weyl, Methoden der organischen Chemie [Methods of Organic Chemistry], Georg Thieme Verlag.

Protective groups that may still be present in the products obtained in the coupling reaction are then removed by standard procedures. For example, tert-butyl protecting groups, in particular a tert-butoxycarbonyl group which is a protected form of an amino group, can be deprotected, i. e. converted into the amino group, by treatment with trifluoroacetic acid. As already explained, after the coupling reaction also functional groups can be generated from suitable precursor groups. In addition, a conversion into a physiologically tolerable salt or a prodrug of a compound of the formula I can then be carried out by known processes.

In general, a reaction mixture containing a final compound of the formula I or an intermediate is worked up and, if desired, the product is then purified by customary processes known to those skilled in the art. For example, a synthesized compound can be purified using well known methods such as crystallization, chromatography or reverse phase-high performance liquid chromatography (RP-HPLC) or other methods of separation based, for example, on the size, charge or hydrophobicity of the compound. Similarly, well known methods such as NMR, IR and mass spectrometry (MS) can be used for characterizing a compound of the invention.

The reactions described above and below that are carried out in the syntheses of the compounds of the formula I can generally be carried out according to the methods of conventional solution phase chemistry. Preferred methods include, but are not limited to those described in the examples.

The compounds of the present invention inhibit the initial step of the thrombogenesis. In particular, they are inhibitors of the interaction between the platelet surface glycoprotein GPIb complex and the plasma protein von Willebrand factor and preferably do not show an essential modulation of the chemokine receptor activity as e.g. measured in a CCR-1 and/or CCR-5 binding assay as disclosed e.g. in Van Riper et al. (1993) J. Exp. Med., 177, 851-856 or in a CCR-2 and/or CCR-3 binding assay as disclosed in e.g. Daugherty et al. (1996) J. Exp. Med., 183, 2349-2354.

Activity of compounds of the formula I was shown by an Eu based binding assay in which the binding of human von Willebrand factor to an europium (Eu)-chelate-labeled chimeric GPIb-Fc protein was induced by botrocetin. The preparation of the Eu-chelate-labeled chimeric GPIb-Fc protein is described in detail in a patent application (Fukuchi et al., EP1074564). $IC_{50}$ (inhibition for 50%) values of all the compounds of the formula I were less than 100 microM.

In view of their ability to inhibit the interaction between GPIb and vWF the compounds of the formula I are useful pharmacologically active compounds which are suitable, for example, for influencing the platelet aggregation and for the treatment, including therapy and prophylaxis, of diseases such as, for example, cardiovascular disorders, thromboembolic diseases or restenoses.

The invention also relates to the treatment of disease states such as abnormal thrombus formation, myocardial infarction, acute myocardial infarction, unstable angina, acute coronary syndromes, coronary artery disease, reocclusion following coronary thrombolysis, occlusion during thromboplasty, coronary restenosis, thromboembolism, pulmonary embolism, left ventricular dysfunction, secondary prevention of clinical vascular complications in patients with cardiovascular and cerebrovascular disease, acute vessel closure associated with thrombolytic therapy or percutaneous transluminal coronary angioplasty, transient ischemic attacks, stroke, atherosclerosis, comedication to vascular interventional strategies, pathologic thrombus formation occurring in the veins of the lower extremities following abdominal, knee and hip surgery, a risk of pulmonary thromboembolism, or disseminated systemic intravascular coagulatopathy occurring in vascular systems during septic shock, certain viral infections or cancer.

The present invention also relates to pharmaceutical preparations (or pharmaceutical compositions) which contain an effective amount of at least one compound of the formula I and/or its physiologically tolerable salts and/or its prodrugs in addition to a customary pharmaceutically acceptable carrier, i. e. one or more pharmaceutically acceptable carrier substances or excipients and/or auxiliary substances or additives.

The compounds of the formula I and their physiologically tolerable salts and their prodrugs can be administered to animals, preferably to mammals, and in particular to humans as pharmaceuticals for therapy or prophylaxis. They can be administered on their own, or in mixtures with one another or in the form of pharmaceutical preparations which permit enteral or parenteral administration and which contain, as active constituent, an effective amount of at least one compound of the formula I and/or its physiologically tolerable salts and/or its prodrugs and a pharmaceutically acceptable carrier.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula I and/or its (their) physiologically tolerable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula I and/or their physiologically tolerable salts and/or their prodrugs. The amount of the active ingredient of the formula I and/or its physiologically tolerable salts and/or its prodrugs in the pharmaceutical preparations normally is from about 0.5 to about 1000 mg, preferably from about 1 to about 500 mg.

In addition to the active ingredients of the formula I and/or their physiologically acceptable salts and/or prodrugs and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula I and/or their physiologically tolerable salts and/or their prodrugs. In case a pharmaceutical preparation contains two or more compounds of the formula I the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula I allows a great deal of control over the biological and physicochemical properties of the compounds and thus allows the selection of such desired compounds. Furthermore, in addition to at least one compound of the formula I and/or its physiologically tolerable salts and/or its prodrugs, the pharmaceutical preparations can also contain one or more other therapeutically or prophylactically active ingredients.

The present invention also relates to the use of the compound of the formula I for the inhibition of the GPIb-vWF interaction in vitro or in vivo. Consequently, the present invention additionally relates to a method for the inhibition of the GPIb-vWF interaction in a mammal comprising the administration of an effective amount of a compound of formula I in all their stereoisomeric forms and mixtures thereof in any ratio, and their physiologically tolerable salts, as e.g. explained already above.

Provisional application No. 60/416,953 filed Oct. 8, 2002, including the specification, drawings, claims and abstract, is hereby incorporated by reference. All publications cited herein are incorporated in their entireties by reference.

It is understood that modifications that do not substantially affect the activity of the various embodiments of this invention are included within the invention disclosed herein. Accordingly, the following examples are intended to illustrate but not limit the present invention.

EXAMPLES

When in the final step of the synthesis of a compound an acid such as trifluoroacetic acid or acetic acid was used, for example when a compound was purified by chromatography using an eluent which contained such an acid, in some cases, depending on the work-up procedure, for example the details of a freeze-drying process, the compound was obtained partially or completely in the form of a salt of the acid used, for example in the form of the acetic acid salt or trifluoroacetic acid salt.

Example 1

3-(2-Amino-6-methyl-pyrimidin-4-ylamino)-N-(4-amino-2-methyl-quinolin-6-yl)-propionamide

A) 3-Amino-N-(4-amino-2-methyl-quinolin-6-yl)-propionamide

To a solution of 2.18 g (11.55 mmol) of 3-tert-Butoxycarbonylamino-propionic acid in 20 ml of DMF were added 3.78 g (11.55 mmol) TOTU. After 15 min at room temperature 2.0 g (11.55 mmol) of 2-methyl-quinoline-4,6-diamine and 2.66 g (23 mmol) of N-ethylmorpholine were added. After 24 h stirring at room temperature the solution was evaporated and the residue was treated with a saturated aqueous solution of NaHCO$_3$. The aqueous solution was extracted with ethyl acetate. The separated organic layer was dried (Na$_2$SO$_4$) and evaporated. The residue was treated with 20 ml 90% trifluoroacetic acid for 2 h. After evaporation the residue was dissolve in water and extracted with ethyl acetate. The aqueous layer was lyophilized to yield 5.15 g (76%) of the title compound. MS 245.1 (M+1)$^+$.

B) 3-(2-Amino-6-methyl-pyrimidin-4-ylamino)-N-(4-amino-2-methyl-quinolin-6-yl)-propionamide A solution of 0.05 g (0.35 mmol) 2-amino-4-chloro-6-methylpyrimidine, 0.204 mg (0.35 mmol) 3-amino-N-(4-amino-2-methyl-quinolin-6-yl)-propionamide and 0.18 mg (1.39 mmol) diisopropyl ethylamine in 5 ml dimethylacetamide was stirred at 100° C. for 2 h. After evaporation of the solvent the residue was purified by HPLC and lyophilized to yield 45 mg of the title compound. MS 352.3 (M+H)$^+$, $^1$H-NMR (DMSO-d$_6$) δ 2.20 (s, 3H), 2.55 (s, 3H), 2.70 (m, 2H), 3.65 (m, 2H), 6.1 (s, NH), 7.70-7.90 (m, 5H), 8.60-8.80 (br.s., NH), 13.85 (br.s., NH).

Activity: 24.30

Example 2

2-Amino-4-[3-(4-amino-2-methyl-quinolin-6-ylcarbamoyl)-phenylamino]-1,6-dimethyl-pyrimidin-1-ium

A) 3-Amino-N-(4-amino-2-methyl-quinolin-6-yl)-benzamide

The method for compound example 1A) was employed to give 1.97 g (66%) of the title compound. MS 393.2 (M+H)$^+$.

B) 2-Amino-4-chloro-1,6-dimethyl-pyrimidin-1-ium

To a suspension of 1 g (7 mmol) 4-chloro-6-methyl-pyrimidin-2-ylamine in 20 toluene 0.878 g (7 mmol) of sulfuric acid dimethyl ester were added. The mixture was heated to 80° C. and stirred. After 6 h further 0.878 g (7 mmol) of sulfuric acid dimethyl ester were added to the solution. Heating and stirring were continued for another 6 h. A resin was formed which was separated from toluene and dissolved in 20 ml of water. To this solution 1 g of NaI were added and heated to 85° C. After cooling to 20° C. a precipitate was formed which was filtered off and washed with diethyl ether to give 740 mg (37%). MS 158.1 (M)$^+$.

C) 2-Amino-4-[3-(4-amino-2-methyl-quinolin-6-ylcarbamoyl)-phenylamino]-1,6-dimethyl-pyrimidin-1-ium The method for compound example 1B) was employed to give 7.5 mg (6%) of the title compound. MS 414.2 (M+H)$^+$, $^1$H-NMR (DMSO-d$_6$) δ 2.45 (s, 3H), 2.60 (s, 3H), 6.40 (s, 1H), 6.60 (s, 1H), 7.60 (m, 1H), 7.85 (m, 2H), 8.05 (m, 2H), 8.25 (br.s.), 8.70 (br.s.), 8.80 (s, 1H), 10.60 (s, 1H), 13.45 (s, 1H).

Activity: 8.84

Example 3

2-Amino-4-[4-(4-amino-2-methyl-quinolin-6-ylcarbamoyl)-benzylamino]-1,6-dimethyl-pyrimidin-1-ium The method for compound example 2) was also employed for example 3. MS 428.29 (M)$^+$, $^1$H-NMR (DMSO-d$_6$) δ 2.38 (s, 3H), 2.58 (s, 3H), 4.70 (d, 2H), 6.18 (s, NH), 6.60 (s, NH), 7.54 (d, 2H), 7.82 (d, 1H), 8.05 (m, 4H), 8.70 (br.s., NH2), 8.78 (m, 1H), 9.02 (m, 1H), 13.42 br.s., NH).

Activity: 92.10

Example 4

Pyrazine-2-carboxylic acid 4-(4-amino-2-methyl-quinolin-6-ylcarbamoyl)-benzylamide To a solution of 10.5 mg (0.08 mmol) of 2-pyrazinecarboxylic acid in 1 ml of DMF were added 27.9 mg (0.085 mmol) TOTU. After 15 min at room temperature 55 mg (0.085 mmol) of 4-Aminomethyl-N-(4-amino-2-methyl-quinolin-6-yl)-benzamide and 39 mg (0.34 mmol) of N-ethylmorpholine were added. After 24 h stirring at room temperature the solution was evaporated and the residue was treated with acetonitrile and water containing 0.005% trifluoroacetic acid. The precipitate was filtered to give 36.7 mg (71%) of the title compound. MS 413.42 (M+1)$^+$, $^1$H-NMR (DMSO-d$_6$) δ 2.58 (s, 3H), 4.60 (d, 2H), 6.58 (s, NH), 7.55 (d, 2H), 7.81 (d, 1H), 8.00 (m, 3H), 8.65 (br.s., NH2), 8.78 (m, 2H), 8.90 (m, 1H), 9.20 (s, 1H), 9.62 (m, 1H), 10.80 (s, NH), 13.38 (br.s., NH).

Activity: 75.50

Example 5

6-Amino-N-[4-(4-amino-2-methyl-quinolin-6-ylcarbamoyl)-benzyl]-nicotinamide

The method for compound example 4) was employed to give 14.4 mg (27%) of the title compound. MS 427.2 (M+H)$^+$, $^1$H-NMR (DMSO-d$_6$) δ 2.55 (s, 3H), 4.48 (d, 2H), 6.58 (s, NH), 7.50 (d, 1H), 7.58 (d, 2H), 7.82 (m, 2H), 7.96 (d, 1H), 8.05 (m, 3H), 8.20 (m, 1 H), 8.68 (br.s, NH2), 8.78 (s, 1H), 10.7 (s, NH).

Activity: 89.90

Example 6

6-Pyrrolidin-1-yl-pyrazine-2-carboxylic acid 4-(4-amino-2-methyl-quinolin-6-ylcarbamoyl)-benzylamide The method for compound example 4) was employed to give 43.3 mg (75%) of the title compound. MS 482.45

(M+H)+; 1H-NMR (DMSO-d6) δ 1.98 (m, 4H), 2.58 (s, 3H), 3.55 (m, 4H), 4.60 (d, 2H), 6.58 (s, NH), 7.70 (d, 2H), 7.80 (d, 1H), 7.95 (m, 3H), 8.15 (s, 1H), 8.30 (s, 1H), 8.65 (br.s, NH2), 8.75 (m, 1H), 9.18 (m, 1H), 10.62 (s, NH), 13.38 (br.s, NH).
Activity: 47.90

Example 7

2-Amino-4-[(4-{[(4-amino-2-methyl-6-quinolinyl)carbonyl]amino}phenyl)amino]-1,6-dimethylpyrimidin-1-ium A) 4-Amino-N-(4-aminophenyl)-2-methyl-6-quinolinecarboxamide To a solution of 270 mg (1.0 mmol) 4-amino-2-methyl-6-quinolincarboxylic acid, 220 mg (1.1 mmol) 4-t-butoxycarbonylaminoaniline, and 0.56 ml (4.0 mmol) triethylamine in 10 ml DMF was added 4.42 mg (1.0 mmol) BOP reagent. After 1 h stirring at room temperature the solution was evaporated. The residue was dissolved in 1M solution of NaOH and extracted with ethyl acetate and the organic layer was washed with water and brine, dried (MgSO4) and evaporated. The residue was treated with 4M HCl in dioxane at room temperature for 1 h. After evaporation the residue was purified by HPLC and lyophilized to give 86 mg (17%) of the title compound. MS 293.3 (M+H)+

B) 2-Amino-4-[(4-{[(4-amino-2-methyl-6-quinolinyl)carbonyl]amino}phenyl)amino]-1,6-dimethylpyrimidin-1-ium A solution of 26 mg (0.05 mmol) 4-amino-N-(4-aminophenyl)-2-methyl-6-quinolinecarboxamide, 17 mg (0.06 mmol) 2-amino-4-chloro-1,6-dimethyl-pyrimidin-1-ium, and 0.262 ml (0.15 mmol) diisopropyl ethylamine in 1 ml DMF was stirred at room temperature for 1 h. After evaporation of the solvent the residue was purified by HPLC and lyophilized to yield 22 mg (66%) of the title compound. MS 414.3 (M+), 1H-NMR (DMSO-d6) δ 2.40 (s, 3H), 2.60 (s, 3H), 3.44 (s, 3H), 6.25 (s, 1H), 6.65 (s, 1H), 7.79 (br. 4H), 7.88 (d, 1H), 8.25 (br. 1H), 8.25 (br. 1H), 8.35 (d, 1H), 8.95 (s, 1H), 8.99 (s, 1H), 10.38 (br. 1H), 10.53 (s, 1H), 13.56 (s, 1H).
Activity: 7.62

Example 8

2-Amino-4-[(3-{[(4-amino-2-methyl-6-quinolinyl)carbonyl]amino}phenyl)amino]-1,6-dimethylpyrimidin-1-ium A) 4-Amino-N-(3-aminophenyl)-2-methyl-6-quinolinecarboxamide The method for compound 7A) was employed to give the title compound. MS 293.3.

B) 2-Amino-4-[(3-{[(4-amino-2-methyl-6-quinolinyl)carbonyl]amino}phenyl)amino]-1,6-dimethylpyrimidin-1-ium The method for compound 7B) was employed to give the title compound. MS 414.3 (M+), 1H-NMR (DMSO-d6) δ 2.40 (s, 3H), 2.61 (s, 3H), 3.44 (s, 3H), 6.29 (s, 1H), 6.66 (s, 1H), 7.33 (s, 1H), 7.45 (br. 1H), 7.85 (br. 1H), 7.89 (d, 1H), 8.03 (br. 1H), 8.10 (br. 1H), 8.35 (d, 1H), 8.96 (s, 1H), 9.00 (br. 1H), 10.44 (s, 1H), 10.54 (s, 1H), 13.57 (s, 1H)
Activity: 82.60

Example 9

2-Amino-4-[(4-{[(4-amino-2-methyl-6-quinolinyl)carbonyl]amino}benzyl)amino]-1,6-dimethylpyrimidin-1-ium A) 4-Amino-N-[4-(aminomethyl)phenyl]-2-methyl-6-quinolinecarboxamide The method for compound 7A) was employed to give the title compound. MS 307.2

B) 2-Amino-4-[(4-{[(4-amino-2-methyl-6-quinolinyl)carbonyl]amino}benzyl)amino]-1,6-dimethylpyrimidin-1-ium The method for compound 7B) was employed to give the title compound. MS 428.4 (M+), 1H-NMR (DMSO-d6) δ 2.32 (s, 3H), 2.60 (s, 3H), 3.38 (s, 3H), 4.54 (d, 2H), 6.65 (s, 1H), 7.33 (d, 2H), 7.74 (d, 2H), 7.88 (d, 1H), 8.02 (br. 1H), 8.35 (d, 1H), 8.96 (s, 1H), 8.97 (br. 2H), 10.50 (s, 1H), 13.61 (s, 1H)
Activity: 20.10

Example 10

2-Amino-4-[(4-{[(4-amino-2-methyl-6-quinolinyl)carbonyl]amino}benzyl)amino]-6-methylpyrimidine The solution of 27 mg (0.05 mmol) 4-{[(4-amino-2-methyl-6-quinolinyl)carbonyl]amino}benzylamine, 15 mg (0.1 mmol) 2-amino-4-chloro-6-methylpyrimidine, and 0.05 ml (0.3 mmol) diisopropyl ethylamine in 1 ml DMF was stirred at 120° C. for 5 h. After evaporation of the solvent the residue was purified by HPLC and lyophilized to yield 17 mg (51%) of the title compound. MS 414.3 (M+1)+, 1H-NMR (DMSO-d6) δ 2.19 (s, 3H), 2.60 (s, 3H), 4.56 (d, 2H), 5.94 (s, 1H), 6.65 (s, 1H), 7.33 (d, 2H), 7.75 (d, 2H), 7.88 (d, 1H), 8.35 (d, 1H), 8.97 (s, 1H), 8.96-9.01 (m, 2H), 10.51 (s, 1H), 12.30 (br. 1H), 13.60 (br. 1H).
Activity: 68.60

Example 11

4-Amino-N-[4-({[(6-chloro-3-pyridinyl)carbonyl]amino}methyl)phenyl]-2-methyl-6-quinolinecarboxamide To a solution of 27 mg (0.05 mmol) 4-Amino-N-[4-(aminomethyl)phenyl]-2-methyl-6-quinolinecarboxamide, 16 mg (0.1 mmol) 2-chloronicotinic acid, and 0.035 ml (0.25 mmol) triethylamine in 2 ml DMF was added 0.022 ml (0.1 mmol) DPPA and stirred at room temperature for 1 h. After evaporation of the solvent the residue was purified by HPLC and lyophilized to yield 2.7 mg (8%) of the title compound. MS 446.3 (M+1)+, 1H-NMR (DMSO-d6) δ 2.60 (s, 3H), 4.48 (d, 2H), 6.64 (s, 1H), 7.34 (d, 2H), 7.66 (d, 1H), 7.73 (d, 2H), 7.87 (d, 1H), 8.27 (dd, 1H), 8.35 (dd, 1H), 8.87 (s, 1H), 8.94 (s, 1H), 8.98 (br. 2H), 9.29 (t, 1H), 10.47 (s, 1H).
Activity: 42.90

Example 12

4-Amino-2-methyl-N-(4-{[(2-pyridinylcarbonyl)amino]methyl}phenyl)-6-quinolinecarboxamide To a solution of 27 mg (0.05 mmol) 4-amino-N-[4-(aminomethyl)phenyl]-2-methyl-6-quinolinecarboxamide, 7 mg (0.1 mmol) 2-pyridinecarboxylic acid, and 0.028 ml (0.2 mmol) triethylamine in 2 ml DMF was added 36 mg (0.75 mmol) PyBrop and stirred at room temperature for 1 d. After evaporation of the solvent the residue was purified by HPLC and lyophilized to yield 7.4 mg (23%) of the title compound. MS 412.3 (M+1)$^+$, $^1$H-NMR (DMSO-d$_6$) δ 2.60 (s, 3H), 4.47 (d, 2H), 6.64 (s, 1H), 7.33 (d, 2H), 7.60 (m, 1H), 7.70 (d, 2H), 7.86 (d, 1H), 8.00 (t, 1H), 8.04 (t, 1H), 8.35 (d, 1H), 8.65 (m, 1H), 8.94 (s, 1H), 8.98 (br. 2H), 9.32 (t, 1H).
Activity: 58.40

Example 13

4-Amino-N-[4-({[(2-chloro-4-pyridinyl)carbonyl]amino}methyl)phenyl]-2-methyl-6-quinolinecarboxamide To a solution of 27 mg (0.05 mmol) 4-Amino-N-[4-(aminomethyl)phenyl]-2-methyl-6-quinolinecarboxamide, 9 mg (0.1 mmol) 2-chloropyridine-4-carboxylic acid, and 0.07 ml (0.5 mmol) triethylamine in 2 ml dichloromethane was added 90 mg (2.0 mmol) PyBrop and stirred at room temperature for 1 d. After evaporation of the solvent the residue was purified by HPLC and lyophilized to yield 17 mg (74%) of the title compound. MS 446.3 (M+1)$^+$, $^1$H-NMR (DMSO-d$_6$) δ: 2.60 (s, 3H), 4.47 (d, 2H), 6.64 (s, 1H), 7.34 (d, 2H), 7.73 (d, 2H), 7.81 (dd, 1H), 7.87 (d, 1H), 7.91 (s, 1H), 8.35 (dd, 1H), 8.57 (d, 1H), 8.95 (s, 1H), 9.00 (br. 2H), 9.41 (t, 1H), 10.47 (s, 1H).
Activity: 90.10

Example 14

4-Amino-N-[4-({[(3-bromo-5-pyridinyl)carbonyl]amino}methyl)phenyl]-2-methyl-6-quinolinecarboxamide The method for compound 13 was employed to give the title compound. MS 492.2 (M+1)$^+$, $^1$H-NMR (DMSO-d$_6$) δ: 2.62 (s, 3H), 4.39 (d, 2/3H), 4.49 (d, 4/3H), 6.66 (s, 1H), 7.30 (d, 2/3H), 7.37 (d, 4/3H), 7.75 (d, 2H), 7.89 (d, 1H), 8.37 (d, 1H), 8.48 (s, 1H), 8.88 (s, 1H), 8.96 (s, 1H), 8.96 (br. 2H), 9.03 (s, 1H), 9.33 (t, 2/3H), 10.01 (t, 1/3H), 10.49 (s, 2/3H), 10.52 (s, 1/3H).
Activity: 28,80

Example 15

4-Amino-N-[4-({[(3-amino-2-pyrazinyl)carbonyl]amino}methyl)phenyl]-2-methyl-6-quinolinecarboxamide The method for compound 12 was employed to give the title compound. MS 428.4 (M+1)$^+$, $^1$H-NMR (DMSO-d$_6$) δ: 2.61 (s, 3H), 4.45 (d, 2H), 6.65 (s, 1H), 7.34 (d, 2H), 7.72 (d, 2H), 7.84 (d, 1H), 7.88 (d, 1H), 8.22 (d, 1H), 8.36 (d, 1H), 8.96 (br. 2H), 9.28 (t, 1H), 10.47 (s, 1H).
Activity: 54.70

Example 16

4-Amino-N-{4-[(2-pyridinylcarbonyl)amino]phenyl}-2-methyl-6-quinolinecarboxamide The method for compound 12 was employed to give the title compound. MS 398.1 (M+1)$^+$, $^1$H-NMR (DMSO-d$_6$) δ: 2.60 (s, 4/3H), 2.74 (s, 2/3H), 6.65 (s, 2/3H), 6.70 (s, 1/3H), 7.67 (t, 1H), 7.76 (d, 2H), 7.86-7.96 (m, 3H), 8.08 (d, 1H), 8.15 (d, 2/3H), 8.29 (d, 1/3H), 8.36 (d, 2/3H), 8.49 (d, 1/3H), 8.74 (d, 1H), 8.99 (br. 2H), 8.96 (s, 2/3H), 9.17 (s, 1/3H), 10.45 (s, 1/3H), 10.50 (s, 2/3H), 10.63 (s, 1/3H), 10.64 (s, 2/3H).
Activity: 43.20

Example 17

4-Amino-N-{4-[(3-pyridinylcarbonyl)amino]phenyl}-2-methyl-6-quinolinecarboxamide The method for compound 12 was employed to give the title compound. MS 398.1 (M+1)$^+$, $^1$H-NMR (DMSO-d$_6$) δ: 2.60 (s, 3H), 6.65 (s, 1H), 7.57 (dd, 1H), 7.77 (s, 4H), 7.88 (d, 1H), 8.29 (d, 1H), 8.36 (d, 1H), 8.76 (d, 1H), 8.96 (s, 1H), 9.00 (br. 2H), 9.10 (s, 1H), 10.46 (s, 1H), 10.50 (s, 1H).
Activity: 15.00

Example 18

4-Amino-N-(4-{[(2-chloro-3-pyridinyl)carbonyl]amino}phenyl)-2-methyl-6-quinolinecarboxamide The method for compound 12 was employed to give the title compound. MS 432.1 (M+1)$^+$, $^1$H-NMR (DMSO-d$_6$) δ: 2.62 (s, 3H), 6.66 (s, 1H), 7.58 (dd, 1H), 7.72 (d, 2H), 7.79 (d, 2H), 7.89 (d, 1H), 8.09 (dd, 1H), 8.37 (d, 1H), 8.55 (dd, 1H), 8.97 (s, 1H), 9.00 (br. 2H), 10.52 (s, 1H), 10.66 (s, 1H).
Activity: 52.60

Example 19

4-Amino-N-(4-{[(5-bromo-3-pyridinyl)carbonyl]amino}phenyl)-2-methyl-6-quinolinecarboxamide The method for compound 12 was employed to give the title compound. MS 478.0 (M+1)$^+$, $^1$H-NMR (DMSO-d$_6$) δ: 2.60 (s, 3H), 6.65 (s, 1H), 7.77 (s, 4H), 7.87 (d, 1H), 8.36 (d, 1H), 8.53 (m, 1H), 8.90 (d, 1H), 8.99 (br. 2H), 9.06 (d, 2H), 10.51 (s, 1H), 10.52 (s, 1H).
Activity: 20.90

Example 20

4-Amino-N-(4-{[(2-amino-3-pyrazinyl)carbonyl]amino}phenyl)-2-methyl-6-quinolinecarboxamide The method for compound 12 was employed to give the title compound. MS 414.2 (M+1)$^+$, $^1$H-NMR (DMSO-d$_6$) δ: 2.60 (s, 3H), 6.65 (s, 1H), 7.58 (br. 1H), 7.74 (d, 2H), 7.84 (d, 2H), 7.90 (d, 1H), 8.28 (d, 1H), 8.36 (d, 1H), 8.95 (s, 1H), 9.00 (br. 2H), 10.49 (s, 1H), 10.51 (s, 1H).
Activity: 4.41

Example 21

4-Amino-N-(4-{[(2-amino-3-pyridinyl)carbonyl]amino}phenyl)-2-methyl-6-quinolinecarboxamide The method for compound 12 was employed to give the title compound. MS 413.1 (M+1)$^+$, $^1$H-NMR (DMSO-d$_6$) δ: 2.60 (s, 3H), 6.65 (s, 1H), 6.82 (dd, 1H), 7.69 (d, 2H), 7.76 (d, 2H), 7.88 (d, 1H), 8.15 (dd, 1H), 8.24 (d, 1H), 8.36 (d, 1H), 8.96 (s, 1H), 8.98 (br. 2H), 10.37 (s, 1H), 10.50 (s, 1H).
Activity: 34.40

Example 22

4-Amino-N-(4-{[(2-amino-5-pyridinyl)carbonyl]amino}phenyl)-2-methyl-6-quinolinecarboxamide The method for compound 12 was employed to give the title compound. MS 413.1 (M+1)$^+$, $^1$H-NMR (DMSO-d$_6$) δ: 2.60 (s, 3H), 6.65 (s, 1H), 6.74 (d, 1H), 7.73 (s, 4H), 7.88 (d, 1H), 8.12 (d, 1H), 8.35 (d, 1H), 8.58 (d, 1H), 8.96 (s, 1H), 9.00 (br. 2H), 10.12 (s, 1H), 10.47 (s, 1H).
Activity: 11.10

Example 23

4-Amino-N-(4-{[(2-hydroxy-5-pyridinyl)carbonyl]amino}phenyl)-2-methyl-6-quinolinecarboxamide The method for compound 12 was employed to give the title compound. MS 414.2 (M+1)$^+$, $^1$H-NMR (DMSO-d$_6$) δ: 2.63 (s, 3H), 6.42 (d, 1H), 6.54 (br. 1H), 6.67 (s, 1H), 7.71 (d, 2H), 7.76 (d, 2H), 7.90 (d, 1H), 7.98 (d, 1H), 8.20 (br. 1H), 8.37 (d, 1H), 8.98 (s, 1H), 9.00 (br. 2H), 10.01 (s, 1H), 10.49 (s, 1H).
Activity: 42.10

Example 24

4-Amino-N-(4-{[(2-pyrazinyl)carbonyl]amino}phenyl)-2-methyl-6-quinolinecarboxamide The method for compound 12 was employed to give the title compound. MS 399.3 (M+1)$^+$, $^1$H-NMR (DMSO-d$_6$) δ: 2.58 (s, 3H), 6.63 (s, 1H), 7.82 (d, 3H), 7.90 (d, 3H), 8.33 (br. 1H), 8.80 (br. 1H), 8.81 (s, 1H), 8.93 (d, 1H), 9.10 (s, 1H), 9.29 (s, 1H), 10.54 (s, 1H), 10.75 (s, 1H).
Activity: 15.20

Example 25

4-Amino-N-(4-{[(2,3-dichloro-5-pyridinyl)carbonyl]amino}phenyl)-2-methyl-6-quinolinecarboxamide The method for compound 12 was employed to give the title compound. MS 466.1 (M+1)$^+$, $^1$H-NMR (DMSO-d$_6$) δ: 2.61 (s, 3H), 6.65 (s, 1H), 7.75 (d, 2H), 7.79 (d, 2H), 7.88 (d, 1H), 8.36 (d, 1H), 8.62 (d, 1H), 8.90 (d, 1H), 8.97 (br. 3H), 10.53 (s, 1H), 10.57 (s, 1H).
Activity: 22.90

Example 26

4-Amino-N-(4-{[3-(aminosulfonyl)-4-chlorobenzoyl]amino}phenyl)-2-methyl-6-quinolinecarboxamide The method for compound 12 was employed to give the title compound. MS 510.2 (M+1)$^+$, $^1$H-NMR (DMSO-d$_6$) δ: 2.61 (s, 3H), 6.65 (s, 1H), 7.75 (s, 2H), 7.77 (s, 4H), 7.83 (d, 1H), 7.88 (d, 1H), 8.18 (dd, 1H), 8.36 (d, 1H), 8.52 (d, 1H), 8.95 (s, 1H), 8.98 (br. 2H), 10.50 (s, 1H), 10.56 (s, 1H).
Activity: 32.80

Example 27

4-Amino-N-{4-[(3-dimethylaminobenzoyl)amino]phenyl}-2-methyl-6-quinolinecarboxamide The method for compound 12 was employed to give the title compound. MS 440.2 (M+1)$^+$, $^1$H-NMR (DMSO-d$_6$) δ: 2.60 (s, 3H), 6.65 (s, 1H), 6.91 (d, 1H), 7.21 (m, 1H), 7.31 (t, 1H), 7.75 (s, 4H), 7.88 (d, 1H), 8.36 (s, 1H), 8.96 (s, 1H), 9.00 (br. 2H), 10.14 (s, 1H), 10.47 (s, 1H).
Activity: 46.50

Example 28

4-Amino-N-(4-{[(2-methyl-1H-benzimidazol-5-yl)carbonyl]amino}phenyl)-2-methyl-6-quinolinecarboxamide The method for compound 12 was employed to give the title compound. MS 449.5 (M+1)$^+$, $^1$H-NMR (DMSO-d$_6$) δ: 2.60 (s, 3H), 2.67 (s, 3H), 6.65 (s, 1H), 7.72 (d, 1H), 7.76 (d, 2H), 7.79 (d, 2H), 7.88 (d, 1H), 7.94 (d, 1H), 8.23 (s, 1H), 8.97 (s, 1H), 9.00 (br. 2H), 10.35 (s, 1H), 10.49 (s, 1H).
Activity: 9.56

Example 29

4-Amino-N-(4-{[4-(4-piperidinyloxy)benzoyl]amino}phenyl)-2-methyl-6-quinolinecarboxamide The method for compound 12 was employed to give the title compound. MS 496.2 (M+1)$^+$, $^1$H-NMR (DMSO-d$_6$) δ: 1.84 (br. 2H), 2.09 (br. 2H), 2.61 (s, 3H), 3.11 (br. 2H), 3.23 (br. 2H), 4.77 (br. 1H), 6.65 (s, 1H), 7.12 (d, 1H), 7.76 (s, 4H), 7.89 (d, 2H), 7.96 (d, 2H), 8.36 (d, 1H), 8.53 (br. 2H), 9.02 (br. 3H), 10.12 (s, 1H), 10.49 (s, 1H).
Activity: 19.80

Example 30

4-Amino-N-(4-{[(2-amino-1H-benzimidazol-5-yl)carbonyl]amino}phenyl)-2-methyl-6-quinolinecarboxamide The method for compound 12 was employed to give the title compound. MS 452.3 (M+1)$^+$, $^1$H-NMR (DMSO-d$_6$) δ: 2.61 (s, 3H), 6.65 (s, 1H), 7.45 (d, 1H), 7.77 (s, 4H), 7.85 (d, 1H), 7.88 (d, 1H), 7.92 (s, 1H), 8.36 (d, 1H), 8.63 (br. 2H), 8.96 (s, 1H), 9.00 (br. 2H), 10.31 (s, 1H), 10.49 (s, 1H).
Activity: 4.03

Example 31

4-Amino-N-(4-{[(2-amino-1,2-benzthiazol-6-yl)carbonyl]amino}phenyl)-2-methyl-6-quinolinecarboxamide The method for compound 12 was employed to give the title compound. MS 469.3 (M+1)$^+$, $^1$H-NMR (DMSO-d$_6$) δ: 2.61 (s, 3H), 6.65 (s, 1H), 7.40 (d, 1H), 7.77 (s, 4H), 7.82-7.93 (m, 2H), 8.28 (s, 1H), 8.37 (d, 1H), 9.02 (br, 2H), 9.07 (s, 1H), 10.14 (s, 1H), 10.50 (s, 1H).
Activity: 2.90

Example 32

4-amino-N-{4-[(1H-benzimidazol-5-ylcarbonyl)amino]phenyl}-2-methyl-6-quinolinecarboxamide The method for compound 12 was employed to give the title compound. MS 437.3 (M+1)$^+$, $^1$H-NMR (DMSO-d$_6$) δ: 2.63 (s, 3H), 6.68 (s, 1H), 7.79-7.92 (m, 6H), 8.34 (s, 1H), 8.39 (d, 1H), 8.64 (br. 1H), 8.99 (s, 1H), 9.01 (br. 2H), 10.33 (s, 1H), 10.51 (s, 1H).
Activity: 7.50

Example 33

4-Amino-N-(4-{[(2-amino-6-quinolinyl)carbonyl]amino}phenyl)-2-methyl-6-quinolinecarboxamide The method for compound 12 was employed to give the title compound. MS 463.3 (M+1)$^+$, $^1$H-NMR (DMSO-d$_6$) δ: 2.61 (s, 3H), 6.66 (s, 1H), 7.15 (d, 1H), 7.80 (d, 2H), 7.85 (d, 2H), 7.93 (d, 1H), 8.29 (d, 1H), 8.40 (d, 1H), 8.45 (d, 1H), 8.54 (s, 1H), 9.05 (br. 1H), 9.10 (br. 1H), 9.25 (s, 1H), 10.48 (s, 1H), 10.60 (s, 1H).
Activity: 1.70

Example 34

4-Amino-N-(4-{[(2-amino-6-quinolinyl)carbonyl]amino}-2-methoxyphenyl)-2-methyl-6-quinolinecarboxamide The method for compound 12 was employed to give the title compound. MS 493.2 (M+1)$^+$, $^1$H-NM (DMSO-d$_6$) δ: 2.60 (s, 3H), 3.85 (s, 3H), 6.65 (s, 1H), 7.11 (d, 1H), 7.45 (d, 1H), 7.67 (s, 1H), 7.73 (dd, 2H), 7.88 (d, 1H), 8.26 (d, 1H), 8.40 (d, 2H), 8.52 (s, 1H), 8.95 (br. 2H), 9.01 (s, 1H), 9.64 (s, 1H), 10.48 (s, 1H).
Activity: 3.61

Example 35

4-Amino-N-(2-methoxy-4-{[(2-methyl-1H-benzimidazol-5-yl)carbonyl]amino}phenyl)-2-methyl-6-quinolinecarboxamide The method for compound 12 was employed to give the title compound. MS 481.3 (M+1)$^+$, $^1$H-NMR (DMSO-d$_6$) δ: 2.60 (s, 3/2H), 2.68 (s, 3/2H), 3.78 (s, 3/2H), 3.85 (s, 3/2H), 6.64 (s, 1/2H), 6.65 (s, 1/2H), 7.13 (dd, 1H), 7.44 (dd, 1H), 7.47 (s, 1/2H), 7.48 (s, 1/2H), 7.59 (s, 1/2H), 7.62 (s, 1/2H), 7.70 (m, 1H), 7.72 (s, 1/2H), 7.75 (1/2H), 7.86 (dd, 1H), 7.95 (s, 1/2H), 7.97 (s, 1/2H), 8.25 (s, 1H), 8.37 (t, 2H) m 8.99 (br. 1H), 9.57 (s, 1H), 9.63 (s, 1H), 10.00 (s, 1H), 10.38 (s, 1H).
Activity: 9.18

Example 36

1,4-Di-{[(3-amino-2-methylquinolin-6-yl)carbonyl]amino}benzene

The method for compound 12 was employed to give the title compound. MS ? (M+1)$^+$, $^1$H-NMR (DMSO-d$_6$) δ: 2.61 (s, 6H), 6.66 (s, 2H), 7.79 (s, 4H), 7.89 (d, 2H), 8.36 (dd, 2H), 8.96 (s, 1H), 8.97 (s, 1H), 8.99 (br. 4H), 10.52 (s, 2H).
Activity: 1.57

Example 37

4-Amino-N-{4-[(1H-indazol-6-ylamino)methyl]phenyl}-2-methyl-6-quinolinecarboxamide A) N-(4-aminobenzyl)amino-1H-benzimidazole To the solution of 0.145 g (0.98 mmol) of 4-nitrobenzaldehyde in 3 ml of dichloromethane was added 0.31 g (1.47 mmol) of sodium triacetoxyborohydride, 0.6 ml (0.98 mmol) of acetic acid and 0.13 g (0.98 mmol) of 6-aminoindazole. After stirring the mixture overnight at room temperature, the solvent was evaporated. The resulting residue was dissolved in 10 ml of ethanol, 20 mg of 10% palladium on carbon was added and stirred under hydrogen atmosphere overnight. The catalyst was filtered off through celite. After evaporation of the solvent the residue was purified by HPLC and lyophilized to yield 0.2 g (86%) of the title compound. $^1$H-NMR (CDCl$_3$) δ: 4.12 (2H, br), 6.50-6.70 (5H, m), 7.52 (1H, d), 7.86-7.94 (2H, m), 8.18 (1H, br), 8.29 (1H, br).

B) 4-Amino-N-{4-[(1H-indazol-6-ylamino)methyl]phenyl}-2-methyl-6-quinolinecarboxamide To a solution of 25 mg (0.105 mmol) of N-(4-aminobenzyl)amino-1H-benzimidazole in 1 ml of DMF 35 mg (0.105 mmol) 4-amino-2-methyl-6-quinolinecarboxylic acid, 26 mg (0.137 mmol) of WSC, 21 mg (0.105 mmol) of HOBT and 20 μl (0.105 mmol) of triethylamine were added and the mixture was stirred at room temperature overnight. After the solvent was evaporated, the resulting residue was purified by HPLC and lyophilized to yield 10.2 mg (15%) of the title compound.
MS 423 (M+H)$^+$, $^1$H-NMR (DMSO-d$_6$) δ: 2.63 (3H, br), 4.30 (2H, br), 6.35 (1H, br), 6.67 (2H, m), 7.41 (2H, d), 7.75 (2H, m), 7.90-7.99 (2H, m), 8.35-8.55 (3H, m), 9.05 (3AH, br).
Activity: 2.56

Example 38

4-Amino-N-(4-{[(2-amino-1,3-benzothiazol-6-yl)carbonyl]amino}cyclohexyl)-2-methyl-6-quinolinecarboxamide A) 4-(t-Butoxycarbonylamino)cyclohexylamine To a solution of 1.17 g (10.24 mmol) of trans-1,4-diaminocyclohexane in 60 ml water/THF (1:1) 2.25 g (10.31 mmol) of di-t-butyldicarbonate at 0° C. was added. The mixture was stirred for 1 h at room temperature. After evaporation of the organic solvent, the aqueous phase was extracted with ethyl acetate twice. Combined organic phase was extracted with 0.5N hydrochloric acid. Then the aqueous phase was adjusted to pH 10 with 1 N NaOH solution and extracted with ethyl acetate. The organic phase was washed with brine and dried over anhydrous magnesium sulfate. The solvent was evaporated to yield 138 mg (6.3%) of the title compound. MS 299.4 (M+H+DMSOd$_6$)$^+$ B) 4-Amino-N-(4-aminocyclohexyl)-2-methyl-6-quinolinecarboxamide The method of example 12 using 4-aminoquinolinecarboxylic acid and 4-(t-Butoxy-carbonylamino)cyclohexylamine was employed to give crude 4-Amino-N-[4-(t-butoxycarbonylamino)cyclohexyl]-2-methyl-6-quinolinecarboxamide. The crude compound was treated with 4 N HCl in dioxane for 3 h at room temperature. The solvent was evaporated and the resulting residue was purified by HPLC and lyophilized to yield the title compound. MS 299.4 (M+H)$^+$ C) 4-Amino-N-(4-{[(2-amino-1,3-benzothiazol-6-yl)carbonyl]amino}cyclohexyl)-2-methyl-6-quinolinecarboxamide The method of example 12 was employed to give the title compound. MS 475.4 (M+H)$^+$, $^1$H-NMR (DMSO-d$_6$) δ: 1.46-1.53 (4H, m), 1.96 (4H, br), 2.61 (3H, s), 3.00 (1H, br), 3.82 (1H, br), 6.64 (1H, s), 7.36 (1H, d), 7.75 (1H, d), 7.83

(1H, d), 7.85 (1H, br), 8.15 (1H, d), 8.17 (1H, s), 8.28 (1H, d), 8.42 (1H, d), 8.84 (1H, s), 8.91 (1H, br), 8.97 (1H, br), 13.49 (1H, s).

Activity: 33.3

Example 39

4-Amino-N-(4-{[(2-amino-6-quinolinyl)carbonyl]amino}cyclohexyl)-2-methyl-6-quinolinecarboxamide The method of example 12 was employed to give the title compound. MS 469.4 (M+H)$^+$, $^1$H-NMR (DMSO-d$_6$) δ: 1.53 (4H, br), 1.99 (4H, br), 2.62 (3H, s), 3.00 (1H, br), 3.84 (1H, br), 6.66 (1H, s), 7.12 (1H, d), 7.71 (1H, d), 7.85 (1H, d), 8.19 (1H, d), 8.29 (1H, d), 8.40-8.47 (5H, m), 8.86 (1H, s), 8.92 (1H, br), 8.96 (1H, br), 13.52 (1H, s).

Activity: 28.5

Example 40

Von Willebrand Factor-GPIb Binding Assay

A TBS (Tris buffered saline, 20 mM Tris-HCl (pH 7.4) and 0.15 M NaCl) (50 microl) containing human von Willebrand factor (2.5 microg/ml) was added to each well of 1 96-well plate, and the von Willebrand factor was immobilized as a solid phase overnight at 4 dec. Each well was washed once with TBS (150 microl) and blocked with TBS containing 5% BSA (bovine serum albumin) for about 3 hours. Each well of the plate was washed twice with TBS (150 microl), and then added with 25 microl of an assay buffer (Assay Buffer, 1244-106, produced by Wallac) with the compounds, further added with the assay buffer (25 microl) containing the europium (Eu)-chelate-labeled chimeric GPIb-Fc protein (100 ng/ml), labeled with Eu-N1-ITC (Eu-chelate of N$^1$-(p-isothiocyanatebenzyl)-diethlenetriamine-N$^1$,N$^2$,N$^3$,N$^3$-tetraacetic acid, 1244-302, produced by Wallac) and botrocetin (500 ng/ml), and left stand at room temperature for 2 hours. The preparation of the Eu-chelate-labeled chimeric GPIb-Fc protein is described in detail in a patent application (Fukuchi et al., EP1074564). Each well of the plate was washed 5 times with TBS (150 microl) containing 0.05% Tween-20, then added with 100 microl of a fluorescence enhancement buffer (Enhancement Solution, 1244-104, produced by Wallac), and shaken for 1 minute. Then, the amount of europium (Eu) was measured by using a 1420 ARVO multi-label counter (produced by Wallac, measurements time: 1 second). IC$_{50}$ (inhibition for 50%) values of all the compounds disclosed in this application were less than 100 microM as specified in the examples.

What is claimed is:

1. A compound of the formula I,

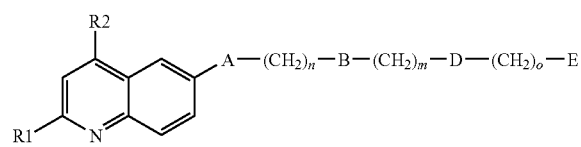

(I)

wherein
n is the integer zero, 1, 2, 3 or 4;
m is the integer zero, 1, 2, 3 or 4;
o is the integer zero, 1, 2, 3 or 4;
R1 is —(C$_1$-C$_8$)-alkyl;
R2 is —NR$^4$R$^5$, wherein
R$^4$ and R$^5$ are identical or different and are hydrogen atom or —(C$_1$-C$_8$)-alkyl;
A is —CO—NH—;
B is 1. a covalent bond,
2. a monocyclic or bicyclic 6- to 14-membered aryl, wherein aryl is unsubstituted or mono-, di-, tri- or tetrasubstituted independently of one another by R$^3$,
3. (C$_3$-C$_8$)-cycloalkyl or
4. Het, wherein Het is unsubstituted or mono-, di-, tri- or tetrasubstituted independently of one another by R$^3$,
D is —NH—;
E is Het, wherein Het is a saturated, partially unsaturated or aromatic monocyclic or bicyclic heterocyclic ring system containing 3 to 10 ring atoms of which 1, 2, 3 or 4 are identical or different heteroatoms selected from the series consisting of nitrogen, oxygen and sulfur and wherein Het is unsubstituted or mono-, di-, tri- or tetrasubstituted independently of one another by R$^3$;
with the proviso that, when B is a covalent bond and Het is a bicyclic heterocyclic ring system, the ring of Het to which D-(CH$_2$)$_o$— is attached contains at least one hetero atom;
R$^3$ is 1. —(C$_1$-C$_8$)-alkyl,
2. (C$_1$-C$_8$)-alkoxy,
3. hydroxyl,
4. trifluoromethoxy,
5. trifluoromethyl,
6. halogen,
7. nitro,
8. —NR$^4$R$^5$, wherein R$^4$ and R$^5$ are as defined above,
9. —(C$_1$-C$_8$)-alkylcarbonyl,
10. —CN,
11. aminosulfonyl-,
12. amidino,
13. guanidino,
14. tri-((C$_1$-C$_4$)-alkyl)ammonio-,
15. di-((C$_1$-C$_8$)-alkyl)amino-,
16. (C$_1$-C$_8$)-alkylaminosulfonyl-,
17. di-((C$_1$-C$_8$)-alkyl)aminosulfonyl,
18. —O-Het, wherein Het is unsubstituted or mono-, di-, tri- or tetrasubstituted independently of one another by R$^3$ and R$^3$ is as defined above under 1. to 17., or
19. Het-, wherein Het is unsubstituted or mono-, di-, tri- or tetrasubstituted independently of one another by R$^3$ and R$^3$ is as defined above under 1. to 17.,
in all their stereoisomeric forms and their physiologically tolerable salts.

2. A compound of the formula I,

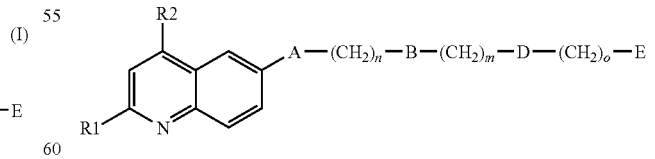

(I)

wherein
n is the integer zero, 1, 2, 3 or 4;
m is the integer zero, 1, 2, 3 or 4;
o is the integer zero, 1, 2, 3 or 4;
R1 is —(C$_1$-C$_8$)-alkyl;
R2 is —NR$^4$R$^5$, wherein $R^4$ and $R^5$ are identical or different and are hydrogen atom or —$(C_1-C_8)$-alkyl;

A is —CO—NH—;

B is 1. a monocyclic or bicyclic 6- to 14-membered aryl, wherein aryl is unsubstituted or mono-, di-, tri- or tetra-substituted independently of one another by $R^3$, 2. $(C_3-C_8)$-cycloalkyl or 3. Het, wherein Het is unsubstituted or mono-, di-, tri- or tetrasubstituted independently of one another by $R^3$, D is —NH—;

E is Het, wherein Het is a saturated, partially unsaturated or aromatic monocyclic or bicyclic heterocyclic ring system containing 3 to 10 ring atoms of which 1, 2, 3 or 4 are identical or different heteroatoms selected from the series consisting of nitrogen, oxygen and sulfur and wherein Het is unsubstituted or mono-, di-, tri- or tetra-substituted independently of one another by $R^3$;

with the proviso that, when B is a covalent bond and Het is a bicyclic heterocyclic ring system, the ring of Het to which D-$(CH_2)_o$— is attached contains at least one hetero atom;

$R^3$ is 1. —$(C_1-C_8)$-alkyl,
2. $(C_1-C_8)$-alkoxy,
3. hydroxyl,
4. trifluoromethoxy,
5. trifluoromethyl,
6. halogen,
7. nitro,
8. —$NR^4R^5$, wherein $R^4$ and $R^5$ are as defined above,
9. —$(C_1-C_8)$-alkylcarbonyl,
10. —CN,
11. aminosulfonyl-,
12. amidino,
13. guanidino,
14. tri-$((C_1-C_4)$-alkyl)ammonio-,
15. di-$((C_1-C_8)$-alkyl)amino-,
16. $(C_1-C_8)$-alkylaminosulfonyl-,
17. di-$((C_1-C_8)$-alkyl)aminosulfonyl,
18. —O-Het, wherein Het is unsubstituted or mono-, di-, tri- or tetrasubstituted independently of one another by $R^3$ and $R^3$ is as defined above under 1. to 17., or
19. Het-, wherein Het is unsubstituted or mono-, di-, tri- or tetrasubstituted independently of one another by $R^3$ and $R^3$ is as defined above under 1. to 17., in all their stereoisomeric forms and their physiologically tolerable salts.

3. A compound of the formula I, as claimed in claim 1, wherein n is the integer zero or 1,
m is the integer zero or 1,
o is the integer zero or 1,
R1 is —$(C_1-C_4)$-alkyl;
R2 is —$NR^4R^5$, wherein
$R^4$ and $R^5$ are identical or different and are hydrogen atom or —$(C_1-C_4)$-alkyl;
A is —CO—NH—;
B is 1. a covalent bond,
2. a monocyclic or bicyclic 6- to 14-membered aryl, wherein aryl is unsubstituted or mono-, di- or trisubstituted independently of one another by $R^3$, or
3. $(C_3-C_7)$-cycloalkyl,
D is —NH—;
E is Het selected from the group aziridine, oxirane, azetidine, pyrrole, furan, thiophene, dioxole, imidazole, pyrazole, oxazole, isoxazole, thiazole, isothiazole, 1,2,3-triazole, 1,2,4-triazole, pyridine, pyran, thiopyran, pyridazine, pyrimidine, pyrazine, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, benzo[1,4]dioxine, 4H-benzo[1,4]oxazine, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines or ring systems which result from the listed heterocycles by fusion or condensation of a carbocyclic ring, for example benzo-fused, cyclopenta-fused, cyclohexa-fused or cyclohepta-fused derivatives of these heterocycles, pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine morpholine), 2,3-dihydrobenzo[1,4]dioxine, indoline, isoindoline, 3,4-dihydro-2H-benzo[1,4]oxazine, perhydro-1,4-thiazine, perhydroazepine, 1,2,3,4-tetrahydroquinoline, 1,2,3,4-tetrahydroisoquinoline and wherein Het is unsubstituted or mono-, di- or trisubstituted independently of one another by $R^3$;

$R^3$ is 1. —$(C_1-C_4)$-alkyl,
2. hydroxyl,
3. halogen,
4. —$NR^4R^5$, wherein $R^4$ and $R^5$ are as defined above,
5. aminosulfonyl-,
6. $(C_1-C_8)$-alkylaminosulfonyl-,
7. di-$((C_1-C_8)$-alkyl)aminosulfonyl,
8. —$(C_1-C_8)$-alkoxy,
9. —O-Het, wherein Het is as defined above and is unsubstituted or mono-, di- or trisubstituted independently of one another by $R^3$ and $R^3$ is as defined above under 1. to 8., or
10. Het-, wherein Het is as defined above and is unsubstituted or mono-, di- or trisubstituted independently of one another by $R^3$ and $R^3$ is as defined above under 1. to 8.

4. A compound of the formula I as claimed in claim 1 or 2, wherein n is the integer zero or 1,
m is the integer zero or 1,
o is the integer zero or 1,
R1 is methyl;
R2 is amino;
A is —CO—NH—;
B is phenyl, wherein phenyl is unsubstituted or mono-, di- or trisubstituted independently of one another by $R^3$,
D is —NH—;
E is Het, which is selected from the group pyridine, pyrimidine, pyrazine, quinoline, benzimidazole, benzothiazole, isoquinoline, chromane, isochromane, cinnoline, quinazoline, quinoxaline, phthalazine, pyridoimidazoles, pyrroline, pyrrolidine, tetrahydropyridine, indazole, piperidine, imidazolidine, 1,3-oxazolidine, 4,5-dihydro-1,3-thiazole, 1,3-thiazolidine, piperazine, indoline, isoindoline, 1,2,3,4-tetrahydroquinoline, 1,2,3,4-tetrahydroisoquinoline and wherein Het is unsubstituted or mono-, di- or trisubstituted independently of one another by $R^3$;

$R^3$ is 1. methyl,
2. hydroxyl,
3. halogen,
4. —$NH_2$,
5. aminosulfonyl-, 6. methoxyl,
7. —O-Het, wherein Het is as defined above and is unsubstituted or mono-, di- or trisubstituted independently of one another by $R^3$ and $R^3$ is as defined above under 1. to 6., or
8. Het-, wherein Het is as defined above and is unsubstituted or mono-, di- or trisubstituted independently of one another by $R^3$ and $R^3$ is as defined above under 1. to 6.

5. A compound of the formula I as claimed in claim 1, wherein the compound of the formula I is 2-Amino-4-[(4-{[(4-amino-2-methyl-6-quinolinyl)carbonyl]amino}phenyl)amino]-1,6-dimethylpyrimidin-1-ium, 2-Amino-4-[(3-{[(4-amino-2-methyl-6-quinolinyl)carbonyl]amino}phenyl)amino]-1,6-dimethylpyrimidin-1-ium, 2-Amino-4-[(4-{[(4-amino-2-methyl-6-quinolinyl)carbonyl]amino}benzyl)amino]-1,6-dimethylpyrimidin-1-ium, 2-Amino-4-[(4-{[(4-amino-2-methyl-6-quinolinyl)carbonyl]amino}benzyl)amino]-6-methylpyrimidine, or 4-Amino-N-{4-[(1H-indazol-6-ylamino)methyl]phenyl}-2-methyl-6-quinolinecarboxamide.

6. A process for the preparation of a compound of the formula I as claimed in claim 1 or 2, which comprises linking the building blocks of the formulae II, III, and IV

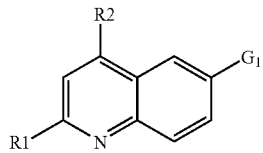

II

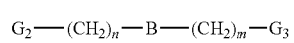

III

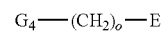

IV by means of forming in a manner known per se an amide bond between the carboxylic acid group G1 depicted in formula II and the $NH_2$ group G2 depicted in formula III or between the carboxylic acid group G2 depicted in formula III and the $NH_2$ group G1 depicted in formula II and by means of forming a bonding between building block of the formula III and building block of the formula IV by nucleophilic substitution of an halogen atom G4 depicted in formula IV by an amino group G3 depicted in formula III or by means of forming a bonding between building block of the formula III and building block of the formula IV by nucleophilic substitution of an halogen atom G3 depicted in formula III by an amino group G4 depicted in formula IV.

7. A pharmaceutical preparation, comprising at least one compound of the formula I as claimed in claim 1 or 2 in all its stereoisomeric forms and mixtures thereof in any ratio and/or its physiologically tolerable salts and a pharmaceutically acceptable carrier.

* * * * *

UNITED STATES PATENT AND TRADEMARK OFFICE
CERTIFICATE OF CORRECTION

PATENT NO.        : 7,745,443 B2                                      Page 1 of 1
APPLICATION NO.   : 11/731978
DATED             : June 29, 2010
INVENTOR(S)       : Klingler et al.

It is certified that error appears in the above-identified patent and that said Letters Patent is hereby corrected as shown below:

Column 10, Line 59, replace "(alkyl)3N$^+$" with -- (alkyl)$_3$N$^+$ --.

Column 19, Line 64, replace "7.33 (s, 1H)" with -- 7.38 (t, 1H) --.

Column 30, lines 19-20, replace "perhydro-1, 4-oxazinemorpholine)" with
    -- perhydro-1,4-oxazine (=morpholine) --.

Signed and Sealed this
Twenty-first Day of February, 2012

David J. Kappos
*Director of the United States Patent and Trademark Office*